United States Patent
Matsuzaki

(10) Patent No.: US 9,898,664 B2
(45) Date of Patent: Feb. 20, 2018

(54) IMAGE PROCESSING DEVICE, IMAGE PROCESSING METHOD, AND INFORMATION STORAGE DEVICE

(71) Applicant: OLYMPUS CORPORATION, Shibuya-ku, Tokyo (JP)

(72) Inventor: Hiroshi Matsuzaki, Tachikawa (JP)

(73) Assignee: Olympus Corporation, Tokyo (JP)

( * ) Notice: Subject to any disclaimer, the term of this patent is extended or adjusted under 35 U.S.C. 154(b) by 67 days.

(21) Appl. No.: 15/012,281

(22) Filed: Feb. 1, 2016

(65) Prior Publication Data

US 2016/0148053 A1 May 26, 2016

Related U.S. Application Data

(63) Continuation of application No. PCT/JP2014/063283, filed on May 20, 2014.

(30) Foreign Application Priority Data

Aug. 2, 2013 (JP) .................................. 2013-161029

(51) Int. Cl.
| | |
|---|---|
| G06K 9/00 | (2006.01) |
| G06T 7/00 | (2017.01) |
| G06T 7/33 | (2017.01) |
| G06T 7/246 | (2017.01) |
| H04N 5/232 | (2006.01) |
| H04N 5/14 | (2006.01) |
| A61B 1/04 | (2006.01) |

(52) U.S. Cl.
CPC ........ *G06K 9/00711* (2013.01); *G06T 7/0016* (2013.01); *G06T 7/246* (2017.01);
(Continued)

(58) Field of Classification Search
CPC ..................................... G06K 9/00; G06T 7/00
(Continued)

(56) References Cited

U.S. PATENT DOCUMENTS

| | | | |
|---|---|---|---|
| 2007/0171279 A1 | 7/2007 | Hasegawa et al. | |
| 2007/0195165 A1* | 8/2007 | Hirakawa .......... | A61B 1/00045 348/75 |

(Continued)

FOREIGN PATENT DOCUMENTS

| | | |
|---|---|---|
| EP | 2006805 A2 | 12/2008 |
| JP | 2006320650 A | 11/2006 |

(Continued)

OTHER PUBLICATIONS

International Search Report (ISR) dated Jul. 8, 2014 issued in International Application No. PCT/JP2014/063283.

(Continued)

*Primary Examiner* — Abolfazl Tabatabai
(74) *Attorney, Agent, or Firm* — Holtz Holtz & Volek PC

(57) ABSTRACT

An image processing device includes a memory and a processor. The processor acquires an image sequence, calculates deformation information about images, performs a feature area detection process, performs an identicalness determination process on an ith feature area and an (i+1)th feature area based on the deformation information about an ith image and an (i+1)th image, and performs an image summarization process. The processor performs the deformation information calculation process that calculates the deformation information based on an ith deformation estimation target area that includes an area of the ith image other than the ith feature area, and an (i+1)th deformation estimation target area that includes an area of the (i+1)th image other than the (i+1)th feature area.

13 Claims, 9 Drawing Sheets

(52) U.S. Cl.
    CPC ............ *G06T 7/33* (2017.01); *A61B 1/041* (2013.01); *G06T 2207/10016* (2013.01); *G06T 2207/10068* (2013.01); *G06T 2207/30028* (2013.01); *G06T 2207/30096* (2013.01)

(58) Field of Classification Search
    USPC ......... 382/103, 128–134, 294; 348/169–172, 348/352
    See application file for complete search history.

(56) References Cited

U.S. PATENT DOCUMENTS

| | | | |
|---|---|---|---|
| 2009/0245692 A1* | 10/2009 | Okutomi | G06T 7/32 382/294 |
| 2010/0119110 A1 | 5/2010 | Kanda | |
| 2010/0183204 A1 | 7/2010 | Kanda | |

FOREIGN PATENT DOCUMENTS

| | | |
|---|---|---|
| JP | 2007257287 A | 10/2007 |
| JP | 2008217714 A | 9/2008 |
| JP | 2009268005 A | 11/2009 |
| JP | 2010113616 A | 5/2010 |
| JP | 2010158308 A | 7/2010 |

OTHER PUBLICATIONS

Extended European Search Report (EESR) dated May 19, 2017, issued in counterpart European Application No. 14831513.8.

Hosoe, et al., "Evaluation of performance of the Omni mode for detecting video capsule endoscopy images: A multicenter randomized controlled trial", Endoscopy International Open, vol. 04, No. 08, Aug. 8, 2016, pp. E878-E882.

* cited by examiner

IMAGE PROCESSING DEVICE, IMAGE PROCESSING METHOD, AND INFORMATION STORAGE DEVICE

CROSS REFERENCE TO RELATED APPLICATION

This application is a continuation of International Patent Application No. PCT/JP2014/063283, having an international filing date of May 20, 2014, which designated the United States, the entirety of which is incorporated herein by reference. Japanese Patent Application No. 2013-161029 filed on Aug. 2, 2013 is also incorporated herein by reference in its entirety.

BACKGROUND

The present invention relates to an image processing device, an image processing method, an information storage device, and the like.

When handling video images or a huge consecutive image sequence, it is advantageous to perform a process that extracts useful images from such a consecutive image sequence to generate a summary image sequence (hereinafter may be referred to as "image summarization process") from the viewpoint of determining an outline of the image sequence in a short time. For example, a capsule endoscope that is normally used at present captures an in vivo image about every 0.5 seconds until the capsule endoscope that has been swallowed is discharged to the outside of the body to obtain an image sequence that includes about 60,000 consecutive images. These images sequentially capture the state inside the digestive tract, and are displayed and observed using a work station or the like to make a diagnosis. However, since it takes a huge amount of time to sequentially observe all of such a large number of images (e.g., about 60,000 images), technology for implementing efficient observation has been desired.

For example, when employing a process that detects a lesion from such an image sequence via image processing, and displays only the images from which the lesion has been detected, since an identical lesion is continuously captured in many cases, an image sequence that includes consecutive images from which an identical lesion has been detected is obtained. If all of these images are displayed, an identical lesion that is captured within different images is necessarily observed repeatedly (i.e., it is time-consuming) Therefore, an efficient display method (e.g., a method that summarizes an image sequence in which an identical lesion is captured to obtain an image sequence that includes a smaller number of images) has been desired from the viewpoint of labor-saving.

A method that determines whether or not the object captured within each of a plurality of time-series images is identical is known. For example, JP-A-2008-217714 discloses a tracking device that includes an object detection means that detects an object from input image information, a distance-position measurement means that measures the distance and the position of the object relative to the imaging means when the object has been detected by the object detection means, a moving range acquisition means that acquires the moving range per frame relative to the object, and a determination means that determines whether or not the object detected in each frame is identical from the moving range acquired by the moving range acquisition means.

JP-A-2009-268005 discloses an intrusion object detection-tracking device that measures the disappearance time when the current intrusion object that is determined to be identical to the intrusion object has not been detected, maintains the estimated intrusion object state (estimated position and estimated geometrical feature quantity) of the preceding intrusion object to be the estimated intrusion object state of the current intrusion object when the disappearance time is equal to or shorter than the disappearance confirmation time set in advance, and performs an identicalness determination process on the intrusion object detected from the subsequent image data using the estimated position and the estimated geometrical feature quantity.

According to JP-A-2008-217714, the moving range of the target object is estimated, and the identicalness determination process is performed based on whether or not an object having similar characteristics has been captured within the estimated moving range. According to JP-A-2009-268005, the object position is estimated by linear approximation from the history of the object area during a period in which the target object was detected during a period in which the target object is not detected, and the identicalness determination process is performed based on the estimation results.

The technique disclosed in JP-A-2008-217714 and the technique disclosed in JP-A-2009-268005 are designed on the assumption that the target object and the object captured as a background of the target object are rigid and move independently.

SUMMARY

According to one aspect of the invention, there is provided an image processing device comprising:

a memory that stores information; and a processor that operates based on the information stored in the memory, the processor comprising hardware, the processor being configured to implement:

an image sequence acquisition process that acquires an image sequence that includes first to Nth (N is an integer equal to or larger than 2) consecutive images;

a deformation information calculation process that calculates deformation information that represents deformation between two images included in the image sequence;

a feature area detection process that detects a feature area from each of the first to Nth images;

an identicalness determination process that determines whether or not an ith feature area and an (i+1)th feature area are identical to each other based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;

a summarization process that summarizes the image sequence based on results of the identicalness determination process; and a deformation estimation process that projects the ith feature area onto the (i+1)th image based on the ith feature area and the deformation information h(i, i+1) to calculate an ith deformation area, the processor being configured to implement the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area, and implement the identicalness determination process that determines whether or not the ith feature area and the (i+1)th feature area are identical to each other based on the ith deformation area obtained by the deformation estimation process and the (i+1)th feature area.

In the image processing device,
wherein the processor may be configured to implement the image sequence acquisition process that acquires a plurality of time-series in vivo images as the image sequence, and implement the feature area detection process that detects at least one of a lesion area and an abnormal mucous membrane area within each of the plurality of time-series in vivo images as the feature area.

In the image processing device,
wherein the processor may be configured to implement the deformation information calculation process that calculates the deformation information based on the ith deformation estimation target area that includes at least a normal mucous membrane area within the ith image, and the (i+1)th deformation estimation target area that includes at least the normal mucous membrane area within the (i+1)th image.

In the image processing device,
wherein, when the processor has determined that an identical feature area has not been captured in the identicalness determination process,
the processor may be configured to implement the identicalness determination process that continues a process based on the deformation information corresponding to a given number of images, and performs the identicalness determination process when the feature area has been detected within an image among a preset number of images.

In the image processing device,
wherein, when the processor has determined that the ith feature area and the (i+1)th feature area are not identical to each other since the feature area has not been detected from the (i+1)th image in the identicalness determination process,
the processor may be configured to implement the identicalness determination process that performs the identicalness determination process on the ith feature area and an (i+2)th feature area based on the ith feature area, the (i+2)th feature area, and the deformation information h(i, i+2) about the ith image and an (i+2)th image, the (i+2)th feature area being detected as a result of the feature area detection process performed on the (i+2)th image.

In the image processing device,
wherein the processor may be configured to implement the identicalness determination process that terminates the identicalness determination process on the ith feature area when the identicalness determination section has determined that the ith feature area and an (i+k)th (k is an integer) feature area are not identical to each other, and k≥Th (Th is a given integer), the (i+k)th feature area being detected as a result of the feature area detection process performed on the (i+k)th image, and
the processor may be configured to implement the identicalness determination process that performs the identicalness determination process on the ith feature area and an (i+k+1)th feature area based on the ith feature area, the (i+k+1)th feature area, and the deformation information h(i, i+k+1) about the ith image and an (i+k+1)th image when the identicalness determination section has determined that the ith feature area and the (i+k)th feature area are not identical to each other, and k<Th, the (i+k+1)th feature area being detected as a result of the feature area detection process performed on the (i+k+1)th image.

In the image processing device,
wherein the processor may be configured to implement the deformation information calculation process that calculates a motion vector at at least one position within an image as the deformation information, and the processor may be configured to implement the identicalness determination process that performs the identicalness determination process on the ith feature area and the (i+1)th feature area based on the ith feature area, the (i+1)th feature area, and the inter-image motion vector between the ith image and the (i+1)th image.

In the image processing device,
wherein the processor may be configured to implement the identicalness determination process that performs the identicalness determination process based on at least one piece of information among shape information, color information, texture information, and intra-image position information about an ith deformation area that is an area obtained by projecting the ith feature area onto the (i+1)th image using the deformation information h(i, i+1), and the (i+1)th feature area.

In the image processing device,
wherein the processor may be configured to implement the identicalness determination process that performs the identicalness determination process on the ith feature area and the (i+1)th feature area based on reliability of the deformation information h(i, i+1).

In the image processing device,
wherein the processor may be configured to implement the summarization processing process that includes:
an image group setting process that sets an identical feature area image group that includes images among the first to Nth images for which it has been determined that an identical feature area is captured based on the results of the identicalness determination process; and
a summary image sequence generation process that generates a summary image sequence by selecting at least one representative image from the identical feature area image group that has been set by the image group setting process.

In the image processing device,
wherein the processor may be configured to implement the summarization processing process that selects the representative image based on at least one piece of information among area information about the feature area, color information about the feature area, texture information about the feature area, intra-image position information about the feature area, and reliability information about the feature area detection process that correspond to each image included in the identical feature area image group.

According to another aspect of the invention, there is provided an image processing method comprising:
acquiring an image sequence that includes first to Nth (N is an integer equal to or larger than 2) consecutive images;
performing a deformation information calculation process that calculates deformation information that represents deformation between two images included in the image sequence;
performing a feature area detection process on each of the first to Nth images;
performing an identicalness determination process on an ith feature area and an (i+1)th feature area based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;
performing an image summarization process on the image sequence based on results of the identicalness determination process;

performing the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area; and performing a deformation estimation process that projects the ith feature area onto the (i+1)th image based on the ith feature area and the deformation information h(i, i+1) to calculate an ith deformation area, and performing the identicalness determination process on the ith feature area and the (i+1)th feature area based on the ith deformation area obtained by the deformation estimation process and the (i+1)th feature area.

According to another aspect of the invention, there is provided a computer-readable storage device with an executable program stored thereon, wherein the program instructs a microprocessor to perform the following steps of:

acquiring an image sequence that includes first to Nth (N is an integer equal to or larger than 2) consecutive images;

performing a deformation information calculation process that calculates deformation information that represents deformation between two images included in the image sequence;

performing a feature area detection process that detects a feature area from each of the first to Nth images;

performing an identicalness determination process that determines whether or not an ith feature area and an (i+1)th feature area are identical to each other based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;

performing a summarization process that summarizes the image sequence based on results of the identicalness determination process;

performing the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area; and performing the identicalness determination process that performs a deformation estimation process that projects the ith feature area onto the (i+1)th image based on the ith feature area and the deformation information h(i, i+1) to calculate an ith deformation area, and determines whether or not the ith feature area and the (i+1)th feature area are identical to each other based on the ith deformation area obtained by the deformation estimation process and the (i+1)th feature area.

DESCRIPTION OF EXEMPLARY EMBODIMENTS

Figure 1:
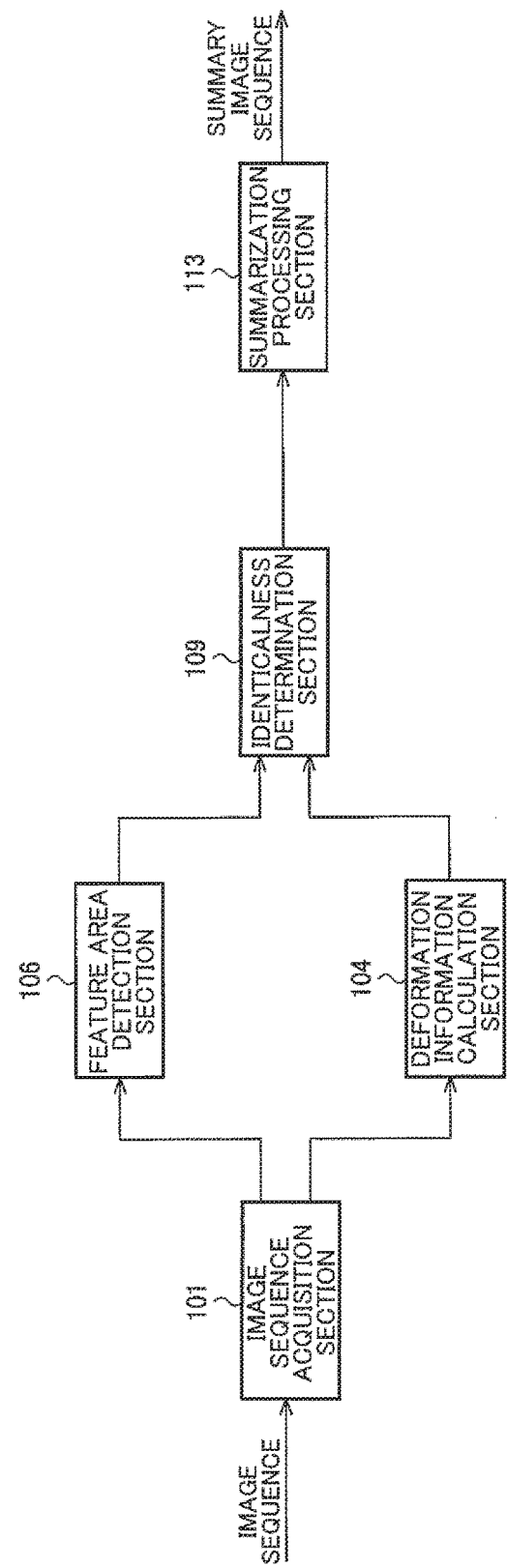
FIG. 1 illustrates a system configuration example of an image processing device according to one embodiment of the invention.

According to one embodiment of the invention, there is provided an image processing device comprising:

a memory that stores information; and a processor that operates based on the information stored in the memory, the processor comprising hardware, the processor being configured to implement:

an image sequence acquisition process that acquires an image sequence that includes first to Nth (N is an integer equal to or larger than 2) consecutive images;

a deformation information calculation process that calculates deformation information that represents deformation between two images included in the image sequence;

a feature area detection process that detects a feature area from each of the first to Nth images;

an identicalness determination process that determines whether or not an ith feature area and an (i+1)th feature area are identical to each other based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;

a summarization process that summarizes the image sequence based on results of the identicalness determination process; and a deformation estimation process that projects the ith feature area onto the (i+1)th image based on the ith feature area and the deformation information h(i, i+1) to calculate an ith deformation area, the processor being configured to implement the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area, and implement the identicalness determination process that determines whether or not the ith feature area and the (i+1)th feature area are identical to each other based on the ith deformation area obtained by the deformation estimation process and the (i+1)th feature area.

According to another embodiment of the invention, there is provided an image processing method comprising:

acquiring an image sequence that includes first to Nth (N is an integer equal to or larger than 2) consecutive images;

performing a deformation information calculation process that calculates deformation information that represents deformation between two images included in the image sequence;

performing a feature area detection process on each of the first to Nth images;

performing an identicalness determination process on an ith feature area and an (i+1)th feature area based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;

performing an image summarization process on the image sequence based on results of the identicalness determination process;

performing the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area; and performing a deformation estimation process that projects the ith feature area onto the (i+1)th image based on the ith feature area and the deformation information h(i, i+1) to calculate an ith deformation area, and performing the identicalness determination process on the ith feature area and the (i+1)th feature area based on the ith deformation area obtained by the deformation estimation process and the (i+1)th feature area.

According to another embodiment of the invention, there is provided a computer-readable storage device with an executable program stored thereon, wherein the program instructs a microprocessor to perform the following steps of:

acquiring an image sequence that includes first to Nth (N is an integer equal to or larger than 2) consecutive images;

performing a deformation information calculation process that calculates deformation information that represents deformation between two images included in the image sequence;

performing a feature area detection process that detects a feature area from each of the first to Nth images;

performing an identicalness determination process that determines whether or not an ith feature area and an (i+1)th feature area are identical to each other based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;

performing a summarization process that summarizes the image sequence based on results of the identicalness determination process;

performing the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area; and performing the identicalness determination process that performs a deformation estimation process that projects the ith feature area onto the (i+1)th image based on the ith feature area and the deformation information h(i, i+1) to calculate an ith deformation area, and determines whether or not the ith feature area and the (i+1)th feature area are identical to each other based on the ith deformation area obtained by the deformation estimation process and the (i+1)th feature area.

1. Method

A method used in connection with the embodiments of the invention is described below. It is desirable to perform the image summarization process when an image sequence that includes a large number of temporally or spatially continuous (consecutive) images has been acquired, and the user performs a process (e.g., medical practice (e.g., diagnosis) when the image sequence is an endoscopic image sequence) using the image sequence. This is because the number of images included in the image sequence is very large, and it takes time for the user to check all of the images included in the image sequence to make a determination. Moreover, it is likely that similar images are included in the image sequence, and the amount of information that can be acquired is limited even if such similar images are thoroughly checked.

Specific examples of such an image sequence include an image sequence captured using a capsule endoscope. The capsule endoscope is a capsule-shaped endoscope that includes a small camera, and captures an image at given time intervals (e.g., every 0.5 seconds). Since the capsule endoscope remains inside the body for several hours (or ten or more hours in some cases) until it is discharged from the body, several tens of thousands of captured images are acquired during a single examination. When the capsule endoscope moves inside a living body, the capsule endoscope may stop, or move backward, due to the motion of the living body, for example. Therefore, a large number of captured images may include a number of images that capture a similar object, and are not useful for diagnosis or the like.

The image summarization process may be designed to detect a lesion area from an image, allows an image from which a lesion area has been detected to remain in the summary image sequence, and deletes an image from which a lesion area has not been detected. However, a lesion area may be detected from most of the images included in the acquired image sequence depending on the case. In such a case, since it is determined that most of the images cannot be deleted when the image summarization process is performed based on whether or not a lesion area has been detected, the effect of reducing the number of images is low, and it is difficult to reduce the burden imposed on the user (doctor).

In order to solve the above problem, the embodiments of the invention propose a method that performs an identicalness determination process that determines identicalness between a feature area (i.e., a lesion area or an abnormal mucous membrane area in a narrow sense) within a given image and a feature area within another image, and performs the image summarization process based on the results of the identicalness determination process. More specifically, when it has been determined that the feature areas respectively detected from a plurality of images are identical, at least one of the plurality of images is allowed to remain, and the remaining images are deleted. When it has been determined that each feature area is identical (e.g., identical lesion), and at least one image is allowed to remain, information about the feature area is not lost, and the feature area can be observed using the image sequence obtained by the image summarization process (hereinafter may be referred to as "summary image sequence").

Various identicalness determination methods that determine the identicalness of the object captured within an image are known (see JP-A-2008-217714 and JP-A-2009-268005, for example). However, a known method is not necessarily effective when the method is applied to an in vivo image. A known identicalness determination method (tracking method) is designed on the assumption that the object (detection target) undergoes a rigid deformation. For example, JP-A-2008-217714 and JP-A-2009-268005 disclose a human tracking method that utilizes a security camera or the like. In this case, it is not likely that the captured human significantly changes in shape (contour) between a plurality of images captured at different timings. Specifically, a change in position or size (deformation) within each image mainly occurs, and it is likely that such a change in position or size occurs linearly. Such a deformation is referred herein as "rigid deformation". Therefore, no problem occurs when the moving range estimation method disclosed in JP-A-2008-217714 or the tracking method disclosed in JP-A-2009-268005 (that estimates the object position by linear approximation from the history of the object area) is used.

However, the feature area within an in vivo image is a lesion area or the like that occurs on the surface of tissue (e.g., the mucous membrane of the digestive tract), or adheres to the surface of tissue. Tissue may undergo an elastic deformation due to softness, and may change in shape by making a motion (e.g., intestinal peristalsis). Specifically, since the feature area also undergoes a non-rigid (elastic) deformation instead of a rigid deformation, it is difficult to make an accurate determination using a known identicalness determination method.

Figure 4:
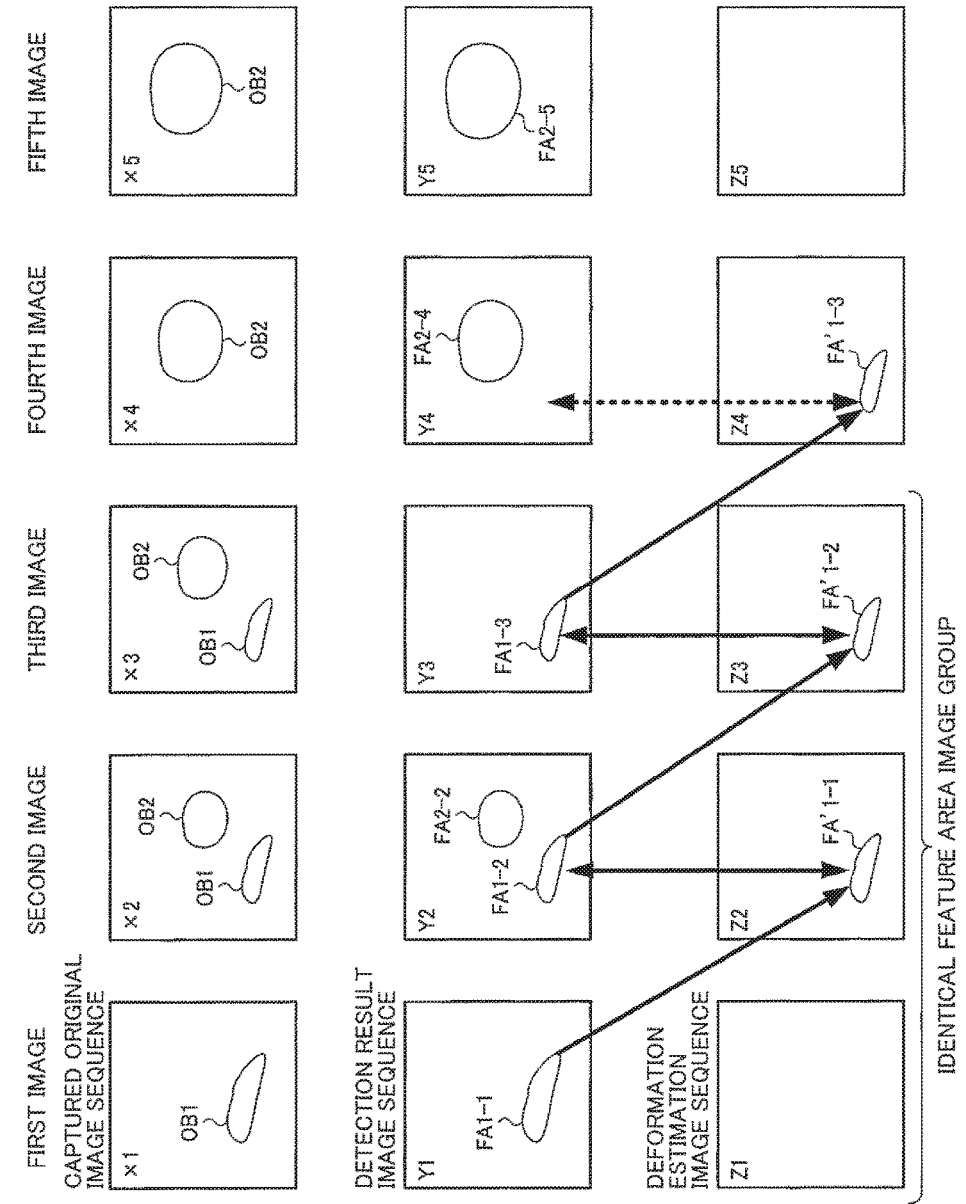
FIG. 4 is a view illustrating a method (first embodiment).

In order to deal with this problem, the embodiments of the invention propose a method that performs a feature area identicalness determination process based on deformation information about a plurality of images (deformation information about deformation between a plurality of images). The deformation information is calculated using at least an area other than the feature area. A known method determines identicalness between a first feature area within a first image and a second feature area within a second image by directly comparing the first feature area and the second feature area. For example, a feature area FA1-1 within an image Y1 illustrated in FIG. 4 is directly compared with a feature area FA1-2 within an image Y2 illustrated in FIG. 4. In this case, when the object undergoes an elastic deformation or the like, the first feature area and the second feature area may significantly differ in shape and the like, and the determination accuracy may deteriorate.

However, since the deformation information includes information about the elastic deformation of the object, it is possible to implement an accurate identicalness determination process even when the identicalness determination process is applied to an in vivo image or the like. For example, a deformation estimation process is performed on the first feature area using the deformation information about the first image and the second image to calculate a deformation area, and the deformation area is compared with the second feature area. In this case, since the deformation between the first image and the second image is canceled (reduced in a broad sense) by the deformation estimation process that utilizes the deformation information, the difference between the deformation area and the second feature area is small when the first feature area and the second feature area are identical to each other, and it is possible to implement an accurate identicalness determination process. For example, a deformation area FA'1-1 within an image Z2 obtained by deforming the feature area FA1-1 within the image Y1 illustrated in FIG. 4 is compared with the feature area FA1-2 within the image Y2.

However, since the above method is designed on the assumption that the deformation information about the images has been calculated with high accuracy, the accuracy of the calculated deformation area and the accuracy of the identicalness determination process that utilizes the deformation area deteriorate if the accuracy of the deformation information is low. It is difficult to obtain accurate deformation information when the deformation information about in vivo images is calculated using only the feature area (lesion area). This is because the feature area within an in vivo image may be screened by the contents, the fold structure, or the like.

For example, the contents (e.g., bubbles and a residue) inside the digestive tract may be captured within an image obtained by capturing the digestive tract (e.g., intestine). If the contents are situated to cover the lesion area, or situated between the lesion area and the imaging section, part or the entirety of the lesion area (that should have been captured) is screened by the contents. A convex structure (e.g., folds) is present within a living body, and may change in position due to a peristalsis and the like. Therefore, even if the lesion area can be captured taking account of only the relative position of the imaging section and the lesion area, the lesion area is captured or screened (i.e., cannot be captured) depending on the motion of the convex structure (e.g., folds).

A low imaging frame rate is normally used when capturing an in vivo image. This particularly applies to a capsule endoscope for which the size of the battery and the device is limited. For example, a frame rate as low as about 2 fps may be used. The accuracy of the deformation information also deteriorates due to such a low frame rate.

In order to deal with the above problem, the deformation information is calculated using at least information about an area of an image other than the feature area (see above). The embodiments of the invention are designed on the assumption that the feature area and an area (i.e., background) other than the feature area make an identical motion within the processing target image. For example, a lesion area (i.e., feature area) within an in vivo image adheres to a mucous membrane area (i.e., background), and the lesion area and the mucous membrane area move (undergo deformation) together. Specifically, the deformation of the mucous membrane area other than the lesion area and the deformation of the lesion area are linked to each other, and it is possible to accurately calculate the deformation information by utilizing the information about the mucous membrane area or the like, even if the lesion area is screened by the contents, the fold structure, or the like.

Figure 3A:
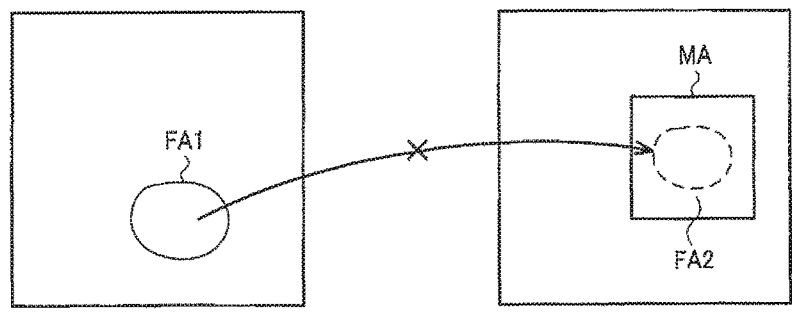
FIGS. 3A to 3C are views illustrating a method that calculates deformation information using an area other than a feature area.
Figure 3B:
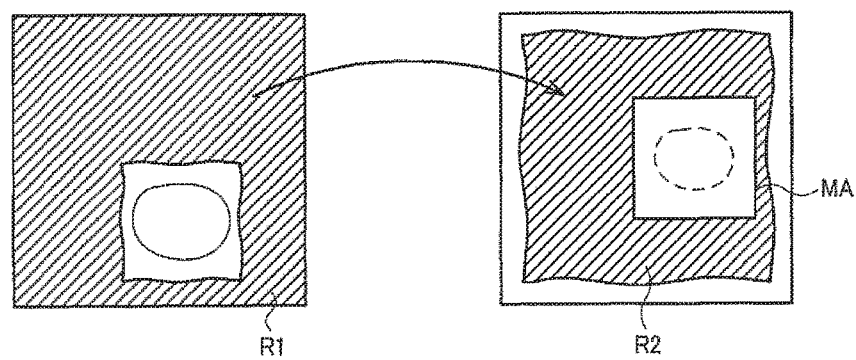
Figure 3C:
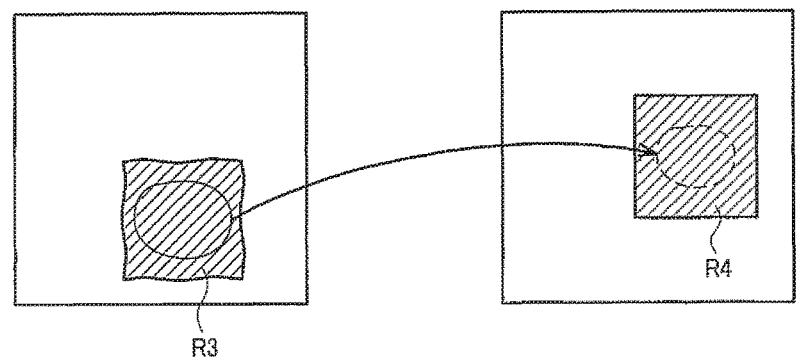

FIGS. 3A to 3C illustrate a specific example. FIG. 3A illustrates an example in which a feature area FA1 was detected within the first image, and an area FA2 within the second image that corresponds to the feature area FA1 was not captured since an area MA that includes the area FA2 was screened by the contents. In this case, the deformation information about the first image and the second image cannot be appropriately calculated using only the information about the feature area FA1 since the area FA2 that is considered to have a feature that corresponds to the feature area FA1 is screened, and an area that corresponds to the feature area FA1 cannot be found from the second image.

In this case, it is possible to find an area within the first image and an area within the second image that corresponds to the area within the first image by calculating the deformation information using the entire image. For example, an area (e.g., mucous membrane area) of the first image other than the lesion area and an area (e.g., mucous membrane area) of the second image other than the lesion area have similar characteristics. Therefore, it is possible to calculate information that represents that an area R1 within the first image corresponds to an area R2 within the second image (see FIG. 3B). It is possible to derive the relationship illustrated in FIG. 3C taking account of the assumption that the feature area and an area other than the feature area undergo deformation together (see above). Specifically, when the area R1 corresponds to the area R2 (see FIG. 3B), an area R3 of the first image other than the area R1 corresponds to an area R4 of the second image other than the area R2 (see FIG. 3C).

It is impossible to derive the relationship illustrated in FIG. 3C using an image to which a known method (see JP-A-2008-217714 JP-A-2008-217714 JP-A-2008-217714 and JP-A-2009-268005, for example) is intended to be applied. This is because the object (e.g., human) (i.e., detection target) and the background (e.g., landscape) move (undergo deformation) independently (see JP-A-2008-217714, for example). For example, even when the relationship between the area R1 and the area R2 has been calculated (see FIG. 3B), an object 1 captured within the area R3 of the first image may move to the outside of the imaging range until the second image is captured, or an object 2 that differs from the object 1 may enter the area R4 until the second image is captured. Alternatively, only one of the object and the background may move, or the object and the background may move in different directions. Therefore, it may be inappropriate to determine that the area R3 corresponds to the area R4, and information about an area other than the feature area may not be effective for deriving the deformation information for calculating the deformation area.

Since the embodiments of the invention are based on the assumption that the lesion area and the mucous membrane area move (make a motion) together, it is natural to derive the relationship between the area R3 and the area R4 based on the relationship between the area R1 and the area R2. Although FIGS. 3A to 3C illustrate the relationship between areas for convenience of explanation, the deformation information may be a motion vector at each point within each image. In this case, the relationship illustrated in FIG. 3B corresponds to a state in which a highly reliable motion vector is calculated at each point included in the area R1, and a motion vector is not calculated (or a motion vector having low reliability is calculated) at each point included in an area (area R3) other than the area R1. The relationship illustrated in FIG. 3C corresponds to a state in which the motion vector at each point included in the area R3 is estimated by performing an interpolation process (correction process) or the like that utilizes the highly reliable motion vector at each point included in the area R1. Specifically, it is possible to accurately calculate (determine) the point (area) within the second image to which an arbitrary point (arbitrary area) within the first image is moved (deformed) using the method according to the embodiments of the invention.

As illustrated in FIG. 1, an image processing device according to the embodiments of the invention includes an image sequence acquisition section 101 that acquires an image sequence that includes first to Nth (N is an integer equal to or larger than 2) consecutive images, a deformation information calculation section 104 that calculates deformation information that represents deformation between two images included in the image sequence, a feature area detection section 106 that performs a feature area detection process on each of the first to Nth images, an identicalness determination section 109 that performs an identicalness determination process on an ith feature area and an (i+1)th feature area based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image, and a summarization processing section 113 that performs an image summarization process on the image sequence based on the results of the identicalness determination process, the deformation information calculation section 104 calculating the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area.

This makes it possible to accurately calculate the deformation information about images. It is also possible to implement an appropriate image summarization process by performing the identicalness determination process using the calculated deformation information.

A first embodiment and a second embodiment are described below. The first embodiment illustrates a basic method, and the second embodiment illustrates a method that deals with a temporary disappearance (non-detection) of the feature area.

2. First Embodiment

Figure 2:
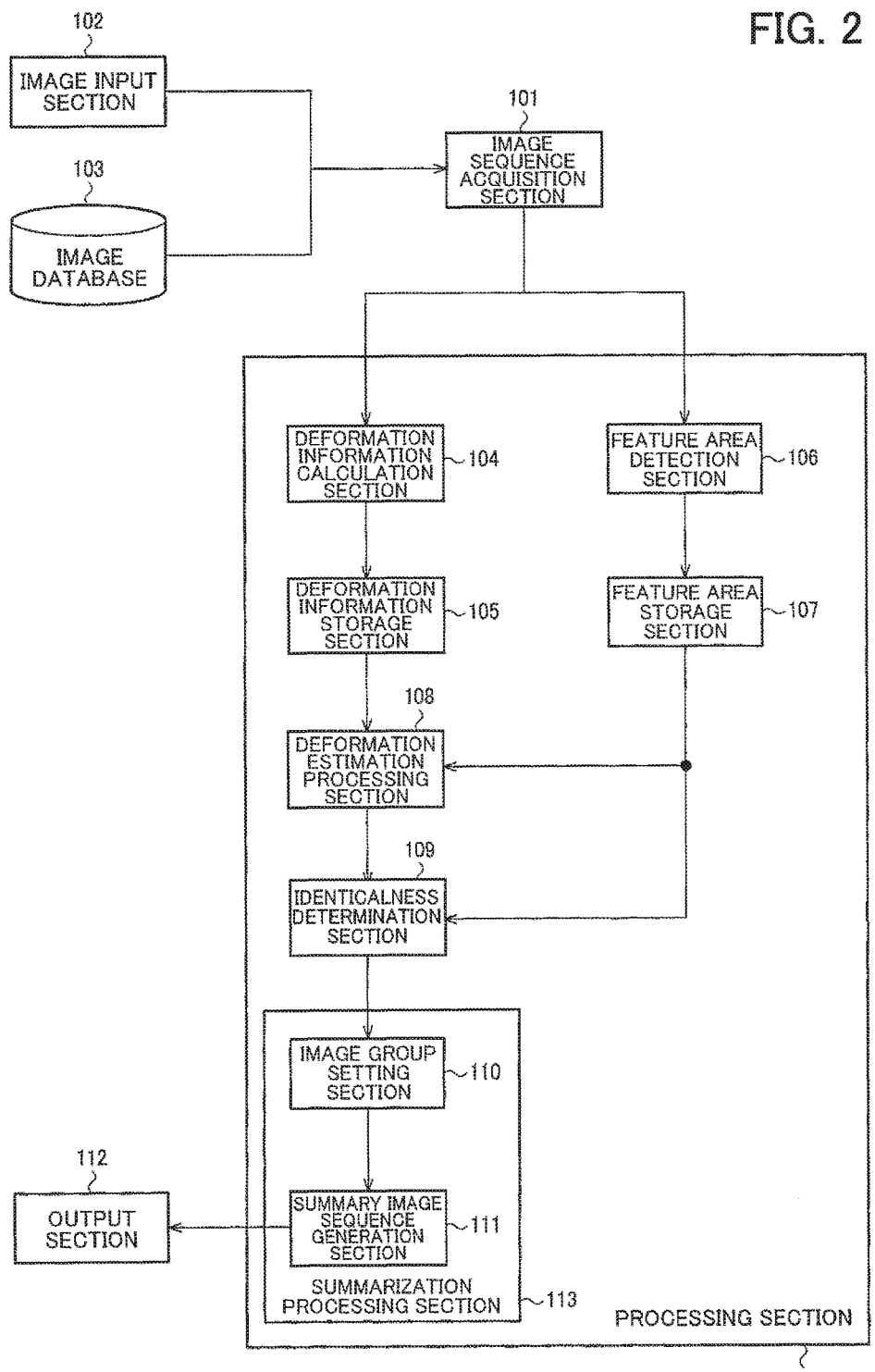
FIG. 2 illustrates a detailed system configuration example of an image processing device according to one embodiment of the invention.

FIG. 2 illustrates a system configuration example of an image processing device according to the first embodiment. The image processing device includes an image sequence acquisition section 101, a processing section 10, and an output section 112. The processing section 10 includes a deformation information calculation section 104, a deformation information storage section 105, a feature area detection section 106, a feature area storage section 107, a deformation estimation processing section 108, an identicalness determination section 109, an image group setting section 110, and a summary image sequence generation section 111. Note that the configuration of the image processing device is not limited to the configuration illustrated in FIG. 2. Various modifications may be made, such as omitting some of the elements illustrated in FIG. 2, or adding other elements. Although FIG. 2 illustrates an example in which an image input section 102 and an image database 103 are provided outside the image processing device, the image processing device may include the image input section 102 and the image database 103.

The image sequence acquisition section 101 acquires an image sequence input from the image input section 102, or an image sequence stored in the image database 103. The term "image sequence" used herein refers to an image sequence that includes a plurality of consecutive images. The term "image sequence" used herein in a narrow sense refers to an image sequence that includes a plurality of in vivo images obtained by capturing the inside of a living body.

The deformation information calculation section 104 calculates deformation information about two images included in the image sequence acquired by the image sequence acquisition section 101. The deformation information calculation section 104 calculates the deformation information using information about the deformation estimation target area that includes at least an area of the image other than the feature area (see above). The detection results of the feature area detection section 106 (described later) may be acquired, and an area of the image other than the detected feature area may be set to be the deformation estimation target area. Note that the configuration is not limited thereto. For example, since it is not likely that the entire in vivo image corresponds to the feature area (lesion area), the entire image may be uniformly set to be the deformation estimation target area. In this case, the deformation information about the first image and the second image is calculated from the entire first image and the entire second image.

The deformation information may be a motion vector at a point within an image. The motion vector can be calculated using various methods such as a block matching method. A deformation parameter between images may be calculated as disclosed in JP-A-2007-257287, and used as the deformation information, or the motion vector calculated based on the deformation parameter may be used as the deformation information. In any case, it suffices that information about an area other than the feature area be used (see FIG. 3B) when calculating the deformation information. The deformation information calculation process can be implemented using various methods. Note that the reliability of the deformation information (e.g., motion vector) may also be calculated when calculating the deformation information.

The deformation information storage section 105 stores the deformation information calculated by the deformation information calculation section 104. As described later with reference to FIG. 4, FIG. 5, FIG. 6 (flowchart), and the like, the process according to the first embodiment can be implemented in a narrow sense using the deformation information about contiguous images. Therefore, the deformation information calculation section 104 may calculate the deformation information about contiguous images included in the image sequence, and the deformation information storage section 105 may store the calculated deformation information. When the image sequence includes first to Nth (N is an integer) images, (N−1) pieces of deformation information are calculated and stored. Note that the process according to the first embodiment need not necessarily be performed on contiguous images. For example, the deformation information about two arbitrary images included in the image sequence may be calculated and stored. In this case, (N(N−1)/2) pieces of deformation information are calculated and stored. Note that the deformation information about two arbitrary images may be calculated using a combination of the deformation information about contiguous images therebetween. For example, deformation information h(s, t) about an sth (s is an integer) image and a tth (t is an integer) image that are not contiguous to each other is calculated using a combination of deformation information h(s, s+1), h(s+1, s+2), . . . , and h(t−1, t) about contiguous images. Specifically, the deformation information about contiguous images may be calculated and stored, and the deformation information about two arbitrary images may be calculated as required.

The feature area detection section 106 detects the feature area from each image included in the image sequence acquired by the image sequence acquisition section 101. The term "feature area" used herein in a narrow sense refers to a lesion area or an abnormal mucous membrane area within an in vivo image. When detecting a lesion or an abnormality on the surface of a mucous membrane, whether to determine a whitish area or a reddish area (e.g., due to bleeding) to be an abnormal area is determined taking account of the target lesion, test items, and the like. Specifically, the detection target can be determined using various methods, and the feature area can be detected using various methods. The feature area need not necessarily be detected based on color (see above), and various modifications are possible. For example, the feature area may be detected using a method that detects a specific lesion area (e.g., epidermoid cancer) based on an image acquired by applying special light (i.e., narrow-band light within a frequency band narrower than that of normal light in a narrow sense), the lesion area detection method disclosed in JP-A-2010-113616 that detects a lesion area within a medical image, or the like.

The feature area storage section 107 stores information about the feature area detected by the feature area detection section 106.

The deformation estimation processing section 108 performs a deformation estimation process that deforms the feature area within a given image, and projects the deformed feature area onto another image based on the deformation information about the images stored in the deformation information storage section 105. The deformation estimation process may be performed on the first feature area that is the feature area within the first image. Note that it suffices that a first deformation area that is an area of the second image that corresponds to the first feature area be calculated as a result of the deformation estimation process, and the deformation estimation process need not necessarily be performed on the first feature area. For example, the entire first image may be deformed based on the deformation information about the first image and the second image, an area of the second image that corresponds to the first image may be calculated, and part of the area of the second image (that corresponds to the first image) that corresponds to the first feature area may be calculated to determine the first deformation area.

The identicalness determination section 109 performs a determination process that determines whether or not the first feature area within the first image and the second feature area within the second image are identical to each other based on the first feature area, the second feature area, and the deformation information about the first image and the second image.

The image group setting section 110 sets a plurality of images that have been determined by the identicalness determination section 109 to include an identical feature area to be an identical feature area image group. When a given feature area has been detected from a given image, and another image that includes a feature area that is determined to be identical to the detected feature area does not exist, it may be determined to allow the given image to remain in the summary image sequence, and the image group setting process may be skipped, or the identical feature area image group may be set to include only the given image.

The summary image sequence generation section 111 performs an image summarization process that selects at least one representative image from the images included in the identical feature area image group set by the image group setting section 110 so that the selected at least one representative image remains in the summary image sequence, and deletes the images that have not been selected as the representative image.

The output section 112 outputs the summary image sequence generated by the summary image sequence generation section 111. The output section 112 may be a display section that displays the images included in the summary image sequence, for example. The summary image sequence may be displayed on an external device other than the image processing device. In this case, the output section 112 outputs the summary image sequence to the external device.

The details of the process according to the first embodiment are described below with reference to FIG. 4. The captured original image sequence (original image sequence) illustrated in FIG. 4 includes images X1 to X5. The detection result image sequence (feature area detection image sequence) illustrated in FIG. 4 that represents the results of the feature area detection process performed on the original image sequence includes images Y1 to Y5. The deformation estimation image sequence (deformation area image sequence) illustrated in FIG. 4 that represents the results of the deformation estimation process performed on the feature area detected from the detection image sequence includes images Z1 to Z5.

In the example illustrated in FIG. 4, an identical object (identical lesion in a narrow sense) OB1 is captured within the images X1 to X3. An object OB2 that differs from the object OB1 is captured within the images X2 to X5.

A feature area FA1-1 that corresponds to the object OB1 has been detected within the image Y1, a feature area FA1-2 that corresponds to the object OB1 and a feature area FA2-2 that corresponds to the object OB2 have been detected within the image Y2, a feature area FA1-3 that corresponds to the object OB1 has been detected within the image Y3, a feature area FA2-4 that corresponds to the object OB2 has been detected within the image Y4, and a feature area FA2-5 that corresponds to the object OB2 has been detected within the image Y5 as a result of the feature area detection process performed on the images X1 to X5. As is clear from a comparison between the image X3 and the image Y3, a feature area that corresponds to the object OB2 may not be detected as a result of the feature area detection process performed on the image X3 in which the object OB2 is captured. Such a situation may occur when the accuracy of the detection process is low, or when the object is screened by the contents or the fold structure, for example.

In the first embodiment, the identicalness determination process is performed on the detected feature areas (see the images Y1 to Y5). A specific example is described below. Whether or not each of the images Y2 to Y5 includes a feature area that is identical to the feature area FA1-1 (starting point) detected within the image Y1 is determined.

In this case, the feature area FA1-1 is not compared directly with the feature area FA1-2 or the feature area FA2-2, for example. In the first embodiment, the deformation estimation process that utilizes the deformation information is performed on the feature area FA1-1. More specifically, the feature area FA1-1 is deformed using the deformation information about the image X1 and the image X2 to calculate the deformation area. A deformation area FA'1-1 included in the image Z2 is calculated by deforming the feature area FA1-1.

The identicalness determination process compares the deformation area FA'1-1 with the feature area detected within the corresponding image. More specifically, the identicalness determination process determines the image Y2 to be an image that corresponds to the image Z2 for which the deformation area FA'1-1 has been calculated, and compares the feature areas FA1-2 and FA2-2 detected within the image Y2 with the deformation area FA'1-1. Specifically, the identicalness determination process is performed on the feature areas FA1-1 and FA1-2 using the deformation area FA'1-1 and the feature area FA1-2, and the identicalness determination process is performed on the feature areas FA1-1 and FA2-2 using the deformation area FA'1-1 and the feature area FA2-2.

The identicalness determination process may be implemented by defining a degree-of-similarity function using the degree of overlap between the deformation area and the feature area, the degree of shape similarity between the deformation area and the feature area, the degree of texture similarity between the deformation area and the feature area, and the like, and comparing the degree of similarity with a threshold value. The processing target feature areas (two feature areas) are determined to be identical to each other when the degree of similarity is larger than the threshold value. Note that the term "degree of shape similarity" used herein refers to information that represents the degree of similarity in contour (that is represented by the edge or the like) of each area, for example. The term "degree of texture similarity" used herein refers to information that represents the degree of similarity in texture (e.g., pattern) within each area. Note that the degree-of-similarity function may be defined using one of the degree of overlap (position information within each image), the degree of shape similarity, the degree of texture similarity, and the like, or may be defined using two or more of the degree of overlap, the degree of shape similarity, the degree of texture similarity, and the like. In the example illustrated in FIG. 4, the feature areas FA1-1 and FA1-2 are determined to be identical to each other since the deformation area FA'1-1 and the feature area FA1-2 are similar to each other. The feature areas FA1-1 and FA2-2 are determined to differ from each other. When a feature area determined to be identical to the feature area used as the starting point has been found, an image that includes a feature area that is identical to the feature area (feature area FA1-1) used as the starting point is continuously searched. This is because an identical feature area may be detected over three or more images.

In this case, the feature area FA1-1 may be deformed, projected onto the third image (Z3), and compared with the feature area detected within the image Y3. According to the first embodiment, however, the deformation information is calculated with high accuracy, but ideal deformation information without an error is not necessarily obtained. The process that deforms and projects the feature area FA1-1 onto the image Z3 corresponds to a process that deforms the feature area FA1-1 using the deformation information h(1, 2) about the image X1 and the image X2 to calculate the deformation area FA'1-1, and deforms the deformation area FA'1-1 using the deformation information h(2, 3). Specifically, since the deformation process performed on non-contiguous images included in the image sequence is implemented by combining the deformation processes using a plurality of pieces of deformation information, an error included in the deformation information is accumulated.

When the feature areas FA1-1 and FA1-2 have been determined to be identical to each other, the process that determines whether or not the feature areas FA1-1 and FA1-3 are identical to each other is the same as the process that determines whether or not the feature areas FA1-2 and FA1-3 are identical to each other. While the deformation area FA'1-1 is an area estimated using the deformation information, the feature area FA1-2 is an area actually detected from the original image X2, and has high reliability.

Therefore, the identicalness determination process performed on a given feature area can be implemented by a process that deforms and projects the latest feature area that has been determined to be identical to the given feature area onto the contiguous image. More specifically, the feature area FA1-2 is deformed using the deformation information h(2, 3) to calculate a deformation area FA'1-2, and the deformation area FA'1-2 is compared with the feature area FA1-3 detected within the image Y3 (see FIG. 4).

In the example illustrated in FIG. 4, the feature areas FA1-2 and FA1-3 are determined to be identical to each other since the degree of similarity between the deformation area FA'1-2 and the feature area FA1-3 is high. The feature area FA1-3 is then deformed using the deformation information h(3, 4) to calculate a deformation area FA'1-3, and the deformation area FA'1-3 is compared with the feature area detected within the image Y4. In the example illustrated in FIG. 4, a feature area that is determined to be identical to the deformation area FA'1-3 is not found within the image Y4, and the process performed on the feature area FA1-1 is terminated.

Since it has been determined by the above process that the first to third images include an identical feature area, the image group setting section 110 sets the first to third images to be the identical feature area image group. The summary image sequence generation section 111 selects at least one image from the identical feature area image group as the representative image. The representative image may be selected from the processing target identical feature area image group using information about the results of an image recognition process or an image detection process (e.g., the size (area) of the feature area, the position of the feature area within the image, color information, texture information, or the reliability of the detection process).

The flow of the process according to the first embodiment is described below with reference to FIG. 6 (flowchart). Note that FIG. 6 (flowchart) illustrates the flow of the feature area identicalness determination process that is performed after the process that calculates the deformation information about the processing target image group and the process that detects the feature area from each image have been performed.

The process is repeatedly performed corresponding to the number of images included in the image sequence (see S301). More specifically, whether or not the feature area has been detected within the processing target image (i) is determined (S302). When the feature area has been detected within the processing target image (i) (Yes in S302), the identicalness determination process (S303 to S306) is performed. When the feature area has not been detected within the processing target image (i) (No in S302) (i.e., when the identicalness determination process using the image (i) as the starting point is unnecessary), the step S301 is performed again after the step S307, and the process is performed on the next image (i+1). In the example illustrated in FIG. 4, since the feature area FA1-1 has been detected within the image Y1 (first image), the steps S303 to S306 that search an image that includes a feature area that is identical to that of the first image are performed.

When the feature area has been detected within the processing target image (i) (Yes in S302), the deformation estimation process that deforms the detected feature area using the deformation information to calculate (estimate) a deformation area (within the contiguous image (i+1)) is performed (S303). The deformation area calculated by the deformation estimation process is compared with the feature area detected within the image (i+1) to determine whether or not the deformation area calculated by the deformation estimation process and the feature area detected within the image (i+1) are identical to each other (S304).

When it has been determined that the deformation area calculated by the deformation estimation process and the feature area detected within the image (i+1) are identical to each other (Yes in S304), the image (i) and the image (i+1) are set to be the identical feature area image group (S305), the value i is incremented (S306), and the step S303 is performed again. Specifically, the deformation estimation process and the identicalness determination process using the image (i) subjected to the step S302 (before the value i is incremented) as the starting point are repeatedly performed on the contiguous images as long as it is determined that the deformation area and the feature area are identical to each other.

When it has been determined that the deformation area and the feature area detected within the contiguous image are not identical to each other (No in S304), the deformation estimation process and the identicalness determination process using the image (i) subjected to the step S302 (before the value i is incremented) as the starting point are terminated, and the step S301 is performed again after the step S307.

Figure 6:
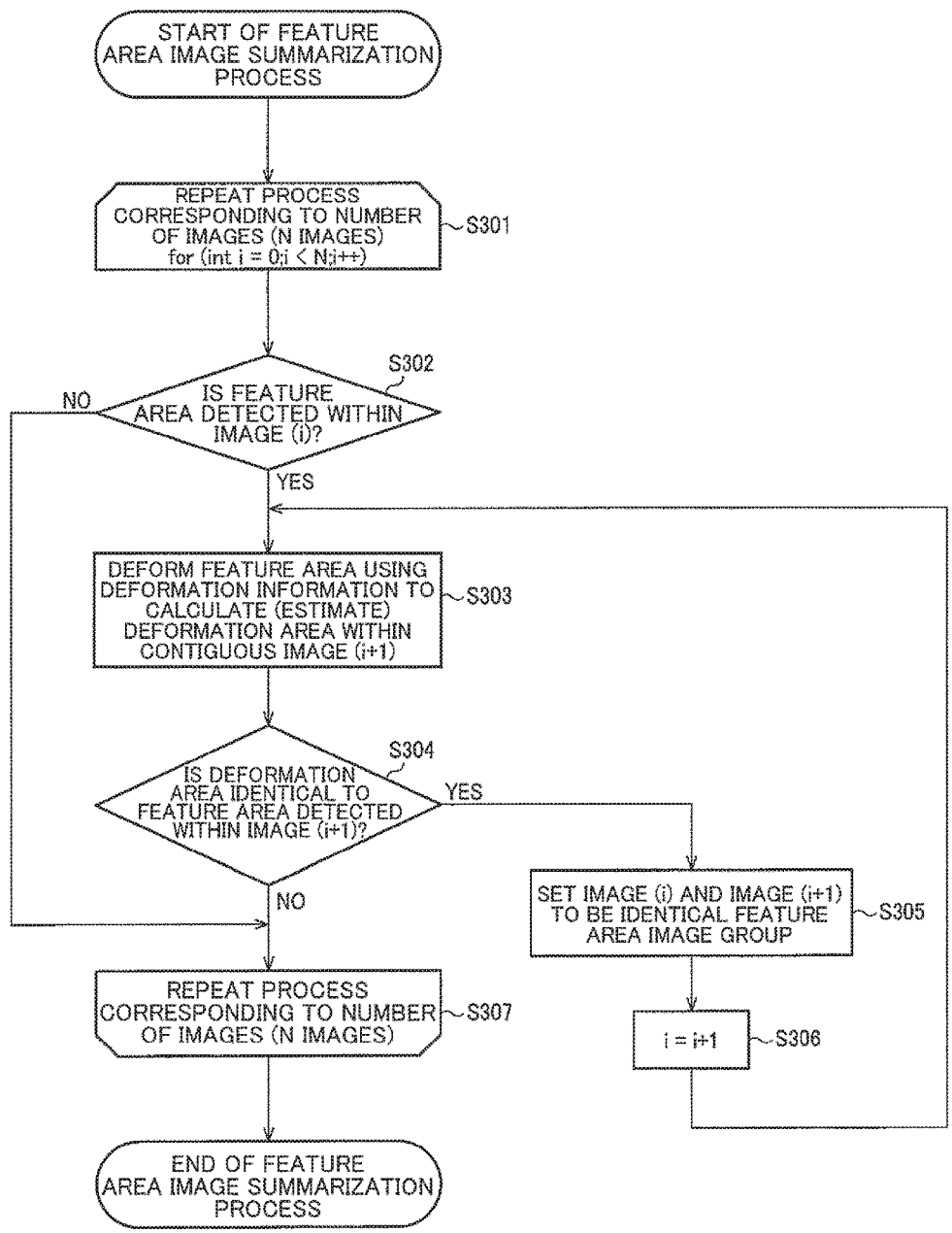
FIG. 6 is a flowchart illustrating a process (first embodiment).

Note that FIG. 6 (flowchart) illustrates an example in which only one feature area is detected from one image. When a plurality of feature areas are detected from one image (see the image Y2 illustrated in FIG. 4, for example), the process is independently performed on each feature area.

In the example illustrated in FIG. 4, the feature areas FA1-2 and FA2-2 have been detected within the second image (image Y2). In this case, the process is independently performed on the feature areas FA1-2 and FA2-2. Since the feature area FA1-2 is determined to be identical to the feature area FA1-1 detected within the first (preceding) image, it is unnecessary to perform the process using the feature area FA1-2 as the starting point.

Figure 5:
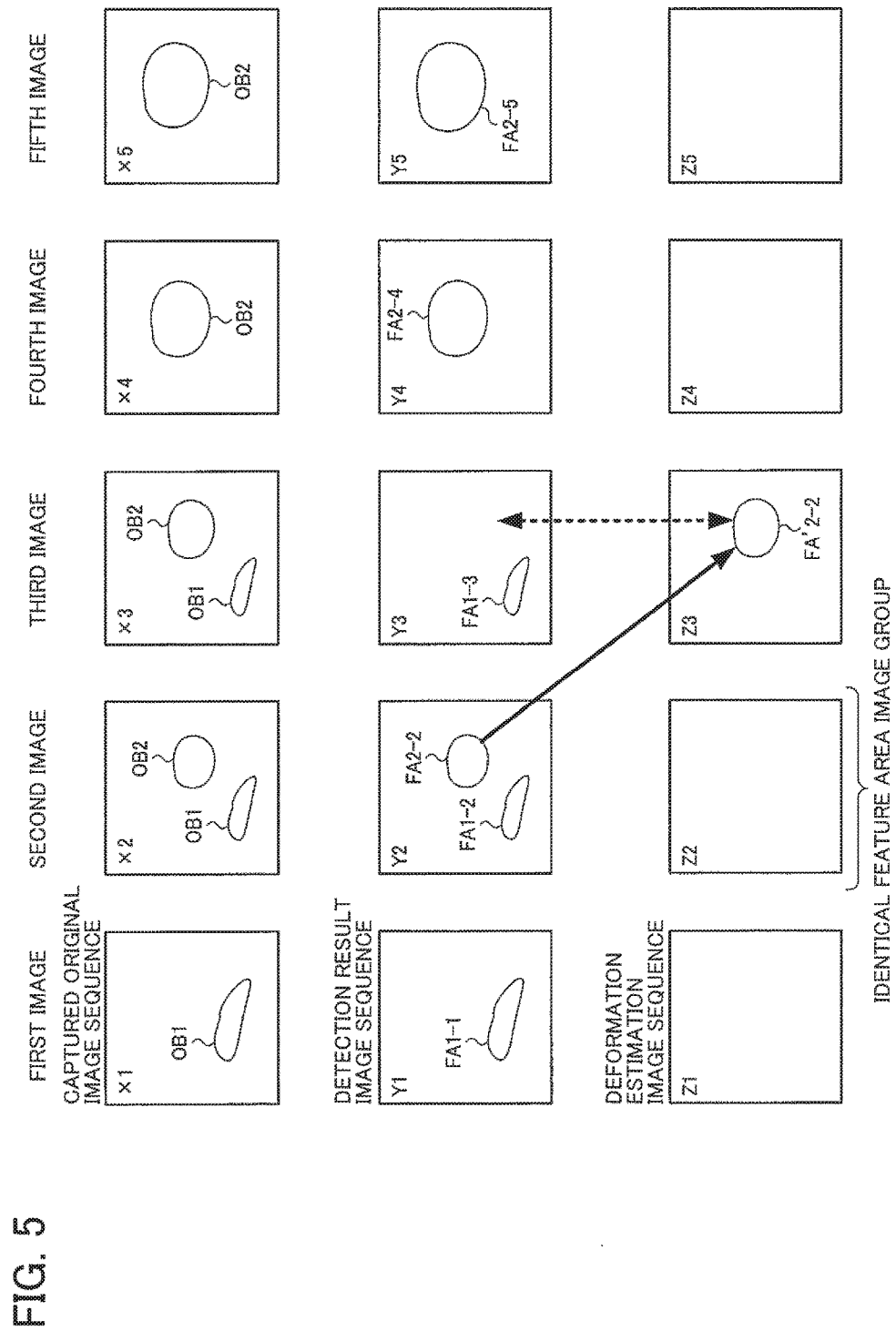
FIG. 5 is another view illustrating a method (first embodiment).

FIG. 5 illustrates an example of the process performed on the feature area FA2-2. As illustrated in FIG. 5, the feature area FA2-2 is deformed using the deformation information h(2, 3) to calculate a deformation area FA'2-2, and the deformation area FA'2-2 is compared with the feature area detected within the image Y3. In the example illustrated in FIG. 5, since the image Y3 does not include a feature area that is determined to be identical to the deformation area FA'2-2, only the second image is set to be the identical feature area image group with regard to the feature area FA2-2. Note that the process that takes account of the feature area FA2-4 detected within the image Y4 and the feature area FA2-5 detected within the image Y5 is described later in connection with the second embodiment.

Figure 7:
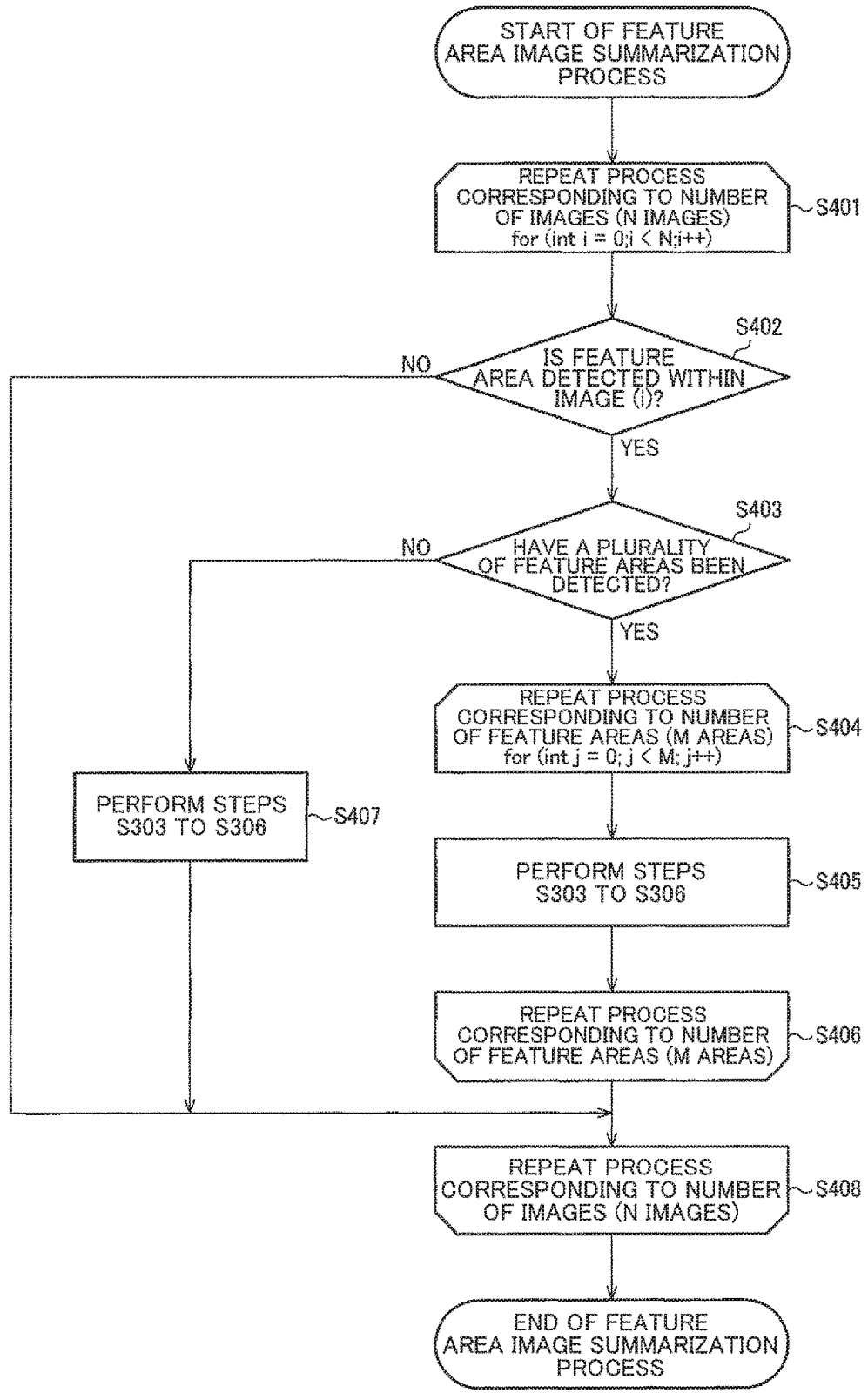
FIG. 7 is another flowchart illustrating a process (first embodiment).

FIG. 7 is a flowchart illustrating an example in which a plurality of feature areas may be detected. Note that steps S401 and S408 illustrated in FIG. 7 are the same as the steps S301 and S307 illustrated in FIG. 6 (i.e., the process is repeated corresponding to the number of images included in the image sequence). The feature area detection process is performed on the processing target image (i) in the same manner as in the step S302 (S402). When the feature area has not been detected (No in S402), the step S401 is performed again after the step S408 (see FIG. 6).

When the feature area has been detected (Yes in S402), whether or not a plurality of feature areas have been detected is determined (S403). When only one feature area has been detected (No in S403), the process is performed in the same manner as illustrated in FIG. 6. Specifically, the process is performed in the same manner as in the steps S303 to S306 illustrated in FIG. 6 (S407).

When a plurality of (M) feature areas have been detected, the process is repeatedly performed on each area (see S404 and S406). The process is performed on each area in the same manner as in the steps S303 to S306 illustrated in FIG. 6 (S405).

When a plurality of feature areas are detected from one image, a plurality of identical feature area image groups may overlap each other (i.e., a given image may be included in both the first identical feature area image group and the second identical feature area image group). In the example illustrated in FIGS. 4 and 5, the first identical feature area image group includes the first to third images, and the second identical feature area image group includes the second image.

In such a case, the representative image may be independently selected from each identical feature area image group. For example, it is possible to observe the object OB1 and the object OB2 using the summary image sequence (i.e., information is not lost) by selecting the first image from the first identical feature area image group as the representative image, and selecting the second image from the second identical feature area image group as the representative image in the example illustrated in FIGS. 4 and 5.

Note that the representative image may be selected taking account of the overlap between the identical feature area image groups. In the example illustrated in FIGS. 4 and 5, the effect of reducing the number of images can be improved by selecting the second image as the representative image since the second image represents both the first identical feature area image group and the second identical feature area image group. Specifically, the representative image may be selected using information about the overlap between a plurality of identical feature area image groups in addition to information about the size (area) of the feature area, the position of the feature area within the image, color information, texture information, the reliability of the detection process, and the like (see above).

According to the first embodiment, the image processing device includes the image sequence acquisition section 101 that acquires an image sequence that includes first to Nth (N is an integer equal to or larger than 2) consecutive images, the deformation information calculation section 104 that calculates the deformation information that represents deformation between two images included in the image sequence, the feature area detection section 106 that performs the feature area detection process on each of the first to Nth images, the identicalness determination section 109 that performs the identicalness determination process on an ith feature area and an (i+1)th feature area based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image, and the summarization processing section 113 that performs the image summarization process on the image sequence based on the results of the identicalness determination process (see FIG. 1). The deformation information calculation section 104 calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area.

The summarization processing section 113 illustrated in FIG. 1 corresponds to the image group setting section 110 and the summary image sequence generation section 111 illustrated in FIG. 2. Note that the summarization processing section 113 may also be implemented by an element other than the image group setting section 110 and the summary image sequence generation section 111.

When displaying only images in which the detection target feature area is captured, it is redundant and troublesome if an identical area is captured within a large number of images. According to the above configuration, it is possible to determine whether or not the detected feature areas are identical, and select an appropriate representative image from the images in which an identical feature area is captured. This makes it possible to improve the effect of reducing the number of images to be displayed, and implement an efficient (less redundant) and effective display process.

When the object undergoes a non-rigid (elastic) deformation, the ith feature area and the (i+1)th feature area in which an identical object is captured may significantly differ in shape and the like. In such a case, it is difficult to determine whether or not the ith feature area and the (i+1)th feature area are identical by directly comparing the ith feature area and the (i+1)th feature area. According to the first embodiment, since it is possible to also take account of an elastic deformation by utilizing the deformation information, an accurate identicalness determination process can be implemented.

According to the first embodiment, the deformation information is calculated using an area of an image other than the feature area (i.e., the entire image in a narrow sense) as the deformation estimation target area. Specifically, when an area other than the feature area is deformed, the feature area included therein is also deformed along with the deformation of the peripheral area, and the deformation area obtained by the deformation process is compared with the detected feature area to implement the identicalness determination process. Since the first embodiment is based on the assumption that the processing target area and the background make an identical motion (i.e., the processing target area adheres to the background), the deformation of the background is useful for estimating the deformation of the feature area.

The image processing device may further include the deformation estimation processing section 108 that performs the deformation estimation process that projects the ith feature area onto the (i+1)th image based on the ith feature area and the deformation information h(i, i+1) to calculate the ith deformation area (see FIG. 2). The identicalness determination section 109 may perform the identicalness determination process on the ith feature area and the (i+1)th feature area based on the ith deformation area obtained by the deformation estimation process and the (i+1)th feature area.

When the ith feature area is the feature area FA1-1 within the image Y1 illustrated in FIG. 4, the ith deformation area corresponds to the deformation area FA'1-1 within the image Z2 illustrated in FIG. 4.

This makes it possible to perform the identicalness determination process on two feature areas by performing the deformation estimation process on one of the feature areas (i.e., the feature area within one image) using the deformation information to calculate the deformation area, and comparing the deformation area and the other feature area (i.e., the feature area within the other image). If the deformation information is ideal information that does no include an error, it is possible to accurately (i.e., without an error) calculate an area in which the object captured within a given area of one image is captured within the other image by performing the deformation estimation process that utilizes the deformation information. Specifically, when the ith feature area and the (i+1)th feature area are identical to each other, it is expected that the ith deformation area and the (i+1)th feature area are ideally identical to each other as to the position, the shape, and the like within the image. Therefore, it is possible to implement the identicalness determination process by performing a simple determination process that determines whether or not two areas are identical to each other, even when the object undergoes an elastic deformation. This makes it possible to implement a highly accurate determination process. Note that two areas are determined to be identical to each other even when the two areas are not exactly identical to each other as long as the two areas are identical to each other to a certain extent, taking account of the fact that it is likely that the deformation information includes an error, and the color information and the texture information may vary depending on the imaging condition (e.g., light intensity) and the like.

The image sequence acquisition section 101 may acquire a plurality of time-series in vivo images as the image sequence. The feature area detection section 106 may detect at least one of a lesion area and an abnormal mucous membrane area within each of the plurality of time-series in vivo images as the feature area.

The term "lesion area" used herein refers to an area within an image that has characteristics that correspond to those of a given lesion. The term "abnormal mucous membrane area" used herein refers to an area that does not correspond to a lesion, but corresponds to a mucous membrane that has characteristics that differ from those of a normal mucous membrane. The feature area detection section 106 may store a model (pattern) that represents a lesion area, and detect a lesion area from an in vivo image. Alternatively, the feature area detection section 106 may store both a model that represents a lesion area and a model that represents an abnormal mucous membrane, and independently detect a lesion area and an abnormal mucous membrane area. Alternatively, the feature area detection section 106 may store a model that represents a normal mucous membrane, and detect an area within an image other than the normal mucous membrane area to be a lesion area or an abnormal mucous membrane area. Note that the detection method implemented by the feature area detection section 106 may be modified in various other ways.

This makes it possible to apply the process according to the first embodiment to an in vivo image, and detect a lesion area or an abnormal mucous membrane area as the feature area. In this case, the lesion area or the abnormal mucous membrane area (i.e., feature area) makes the same motion and undergoes the same deformation as those of a normal mucous membrane area or the like (i.e., an area (background) other than the feature area) together with the normal mucous membrane area or the like. Specifically, it is possible to accurately estimate the deformation of the feature area when the deformation estimation target area that includes an area other than the feature area has been set.

A lesion area or the like within an in vivo image may be screened by the contents (e.g., bubbles or residue), the fold structure of the digestive tract, or the like, and it may be unable to temporarily capture the lesion area or the like. The image quality of an in vivo image captured using a normal medical endoscope apparatus is normally lower than that of an image captured using a normal digital camera or the like since the size of the imaging section is reduced from the viewpoint of invasiveness with respect to patients. Moreover, the imaging frame rate of a capsule endoscope is very low due to limitations to the battery and the like. Since it is very difficult to implement the identicalness determination process (feature area tracking process) that focuses only on the feature area due to these factors, it is advantageous to set the deformation estimation target area to include an area other than the feature area.

In particular, since an image sequence captured using a capsule endoscope includes a large number of similar images, and includes an important feature area (e.g., lesion area or abnormal mucous membrane area), it is desired to improve the inspection (browse) efficiency by displaying only the images from which the feature area has been detected. However, the feature area is detected from a large number of images. Since an identical feature area is captured within a large number of images, it is possible to increase the effect of improving the inspection (browse) efficiency by classifying the images in which an identical feature area is captured into at least one group, and summarizing each group using at least one image. Therefore, the method according to the first embodiment can be effectively applied.

The deformation information calculation section 104 may calculate the deformation information based on the ith deformation estimation target area that includes at least a normal mucous membrane area within the ith image, and the (i+1)th deformation estimation target area that includes at least a normal mucous membrane area within the (i+1)th image.

This makes it possible to set an area that includes a normal mucous membrane area to be the deformation estimation target area. Note that an area other than the feature area (lesion area or abnormal mucous membrane area) may include an area other than a normal mucous membrane area, such as a bubble area, a residue area, an area in which a medicine is scattered, or an area in which inserted forceps or the like is captured (in the case of a normal endoscope apparatus). However, it is highly likely that a normal mucous membrane area is captured within a normal in vivo image, and it is considered that the normal mucous membrane area occupies a large part of the in vivo image. Therefore, it is possible to easily set the deformation estimation target area by utilizing a normal mucous membrane area.

The deformation information calculation section 104 may calculate a motion vector at at least one position within the image as the deformation information. The identicalness determination section 109 may perform the identicalness determination process on the ith feature area and the (i+1)th feature area based on the ith feature area, the (i+1)th feature area, and the inter-image motion vector between the ith image and the (i+1)th image.

This makes it possible to use the motion vector as the deformation information. Note that the deformation information according to the first embodiment is information that represents deformation between images, and is not limited to a motion vector.

The identicalness determination section 109 may perform the identicalness determination process based on at least one piece of information among the shape information, the color information, the texture information, and the intra-image position information about the ith deformation area that is an area obtained by projecting the ith feature area onto the (i+1)th image using the deformation information h(i, i+1), and the (i+1)th feature area.

It may be able to determine the lesion type by the feature area detection process, and lesion type information may also be used for the identicalness determination process. Specifically, the identicalness determination section 109 may perform the identicalness determination process based on at least one piece of information among the shape information, the color information, the texture information, the intra-image position information, and the lesion type information about the ith deformation area that is an area obtained by projecting the ith feature area onto the (i+1)th image using the deformation information h(i, i+1), and the (i+1)th feature area.

This makes it possible to perform the identicalness determination process using the shape information, the color information, the texture information, the intra-image position information, and the like about the deformation area and the feature area as a reference. The identicalness determination process may be performed using the lesion type information together with the above information depending on the situation. Only one piece of information among these pieces of information may be used for the identicalness determination process, or a plurality of pieces of information among these pieces of information may be used for the identicalness determination process. When using a plurality of pieces of information, it is possible to arbitrarily determine whether to equally handle each piece of information or assign high priority to one piece of information. For example, when using a plurality of pieces of information, the identicalness determination process may be performed while setting a degree of importance to each piece of information. More specifically, since it is likely that the feature areas are identical to each other when the feature areas are similar in geometrical position or shape, the shape information and the intra-image position information may be used as the conditions for the identicalness determination process. Even when the feature areas are similar in position or shape, it may be inappropriate to determine that the feature areas are identical to each other when the feature areas differ in texture. Therefore, it is possible to implement a more reliable identicalness determination process by also utilizing the degree of texture similarity as the condition for the identicalness determination process. When using the texture information for the identicalness determination process, it is necessary to deform the texture by texture mapping or the like when the deformation estimation processing section 108 performs the deformation estimation process. In other words, when the texture information is not used for the identicalness determination process, the deformation estimation process may be performed using only the shape (contour).

The identicalness determination section 109 may perform the identicalness determination process on the ith feature area and the (i+1)th feature area based on the reliability of the deformation information h(i, i+1).

According to this configuration, it is possible to implement a more reliable identicalness determination process by also utilizing the deformation information calculation reliability as the condition for the feature area identicalness determination process. This is because the deformation information calculation reliability affects the accuracy of the deformation estimation process.

The summarization processing section 113 may include the image group setting section 110 that sets the identical feature area image group that includes images among the first to Nth images for which it has been determined that an identical feature area is captured based on the results of the identicalness determination process, and the summary image sequence generation section 111 that generates the summary image sequence by selecting at least one representative image from the identical feature area image group that has been set by the image group setting section 110 (see FIG. 2).

This makes it possible to set the identical feature area image group, and summarize the image sequence by selecting the representative image. The identical feature area image group includes the images that respectively include the feature areas that have been determined to be identical to each other. Specifically, the images included in the identical feature area image group overlap each other as to the information about the target feature area. Therefore, it is possible to reduce the number of images while maintaining the information about the target feature area by allowing one image included in the identical feature area image group to remain, and deleting the remaining images. Note that an arbitrary number of images may be selected as the representative image. For example, when diagnosing a lesion area, a plurality of images in which an identical lesion is captured at different angles may be useful. Therefore, a plurality of images may be selected from the identical feature area image group that corresponds to a given feature area as the representative image.

The summarization processing section 113 may select the representative image based on at least one piece of information among the area information about the feature area, the color information about the feature area, the texture information about the feature area, the intra-image position information about the feature area, and the reliability information about the feature area detection process that correspond to each image included in the identical feature area image group.

This makes it possible to select the representative image using at least one aspect among various aspects. For example, an image in which a given lesion area is captured, but the size of the lesion area is very small, or the lesion area is significantly distorted is not considered to be an image that is suitable for observing the lesion area. Likewise, an image in which the lesion area is significantly bright or dark (e.g., blown-out highlights or blocked-up shadows) is also not suitable for observation. Although the method according to the first embodiment reduces the burden imposed on the user (doctor), it is meaningless if sufficient information about the feature area cannot be acquired from the image. Specifically, the representative image may be selected on condition that the feature area is captured with sufficient reliability, or the visibility of the feature area within the image is sufficient, for example.

Note that part or most of the process performed by the image processing device and the like according to the first embodiment may be implemented by a program. In this case, the image processing device and the like according to the first embodiment are implemented by causing a processor (e.g., CPU) to execute a program. Specifically, a program stored in a non-transitory information storage device is read and executed by a processor (e.g., CPU). The information storage device (computer-readable device) stores a program, data, and the like. The function of the information storage device may be implemented by an optical disk (e.g., DVD or CD), a hard disk drive (HDD), a memory (e.g., memory card or ROM), or the like. The processor (e.g., CPU) performs various processes according to the first embodiment based on the program (data) stored in the information storage device. Specifically, a program that causes a computer (i.e., a device that includes an operation section, a processing section, a storage section, and an output section) to function as each section according to the first embodiment (i.e., a program that causes a computer to execute the process implemented by each section according to the first embodiment) is stored in the information storage device.

The image processing device and the like according to the first embodiment may include a processor and a memory. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application-specific integrated circuit (ASIC). The memory stores a computer-readable instruction. Each section of the image processing device and the like according to the first embodiment is implemented by causing the processor to execute the instruction. The memory may be a semiconductor memory (e.g., SRAM or DRAM), a register, a hard disk, or the like. The instruction may be an instruction included in an instruction set that is included in a program, or may be an instruction that causes a hardware circuit included in the processor to operate.

The image processing device may include a memory that stores information (e.g., a program and various types of data), and a processor that operates based on the information stored in the memory. In this case, the processor is configured to implement the process that acquires an image sequence that includes first to Nth (N is an integer equal to or larger than 2) consecutive images, the deformation information calculation process that calculates the deformation information that represents deformation between two images included in the image sequence, the feature area detection process that performs the feature area detection process on each of the first to Nth images, the identicalness determination process that determines whether or not the ith feature area and the (i+1)th feature area are identical to each other based on the ith feature area, the (i+1)th feature area, and the deformation information h(i, i+1) about the ith image and the (i+1)th image, the ith feature area being detected as a result of the feature area detection process performed on the ith image, and the (i+1)th feature area being detected as a result of the feature area detection process performed on the (i+1)th image, the image summarization process that is performed on the image sequence based on the results of the identicalness determination process, and the deformation estimation process that projects the ith feature area onto the (i+1)th image based on the ith feature area and the deformation information h(i, i+1) to calculate the ith deformation area, the processor being configured to implement the deformation information calculation process that calculates the deformation information h(i, i+1) based on the ith deformation estimation target area that includes at least an area of the ith image other than the ith feature area, and the (i+1)th deformation estimation target area that includes at least an area of the (i+1)th image other than the (i+1)th feature area, and implement the identicalness determination process that determines whether or not the ith feature area and the (i+1)th feature area are identical to each other based on the ith deformation area obtained by the deformation estimation process and the (i+1)th feature area.

The processor may implement the function of each section by individual hardware, or may implement the function of each section by integrated hardware, for example. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application specific integrated circuit (ASIC). The memory may be a semiconductor memory (e.g., SRAM or DRAM), a register, a magnetic storage device (e.g., hard disk drive), or an optical storage device (e.g., optical disk device). For example, the memory stores a computer-readable instruction, and each section of the image processing device is implemented by causing the processor to execute the instruction. The instruction may be an instruction included in an instruction set that is included in a program, or may be an instruction that causes a hardware circuit included in the processor to operate.

The operation according to the embodiments of the invention is implemented as described below, for example. The processor acquires an image sequence acquired using a capsule endoscope or the like, and stores the image sequence in the memory. Note that the memory may be the image database 103, and may store the entire image sequence (e.g., 60,000 images). Alternatively, the memory may be an element other than the image database 103, and may acquire part of the image sequence from the image database 103 (e.g., appropriately acquire the processing target image), and store the acquired imaged therein.

The processor may be configured to acquire two images included in the image sequence from the memory, calculate the deformation information h about the two images, and store the calculated deformation information h in the memory. For example, the processor reads contiguous images included in the image sequence from the memory, calculate the deformation information about the images, and store the calculated deformation information in the memory. In this case, the memory corresponds to the deformation information storage section 105.

The processor may be configured to read a given image (ith image) included in the image sequence from the memory, perform the feature area detection process on the image, and store information about the detection result (ith feature area) in the memory. In this case, the memory corresponds to the feature area storage section 107. The processor may be configured to read information about the ith feature area, the (i+1)th feature area, and the deformation information h(i, i+1) from the memory, perform the deformation estimation process that calculates the ith deformation area by projecting the ith feature area onto the (i+1)th image using the information read from the memory, and store the calculated ith deformation area in the memory.

The processor is configured to read the ith deformation area and the (i+1)th feature area from the memory, perform the identicalness determination process on the ith deformation area and the (i+1)th feature area, and perform the image summarization process based on the results of the identicalness determination process. The results of the image summarization process are stored in the memory as the summary image sequence, for example, and the processor reads and outputs the summary image sequence.

Each section of the image processing device is implemented as a module of a program that operates on the processor. For example, the image sequence acquisition section 101 is implemented as an image acquisition module that acquires an image sequence, and writes the acquired image sequence in the memory. Likewise, the deformation information calculation section 104 is implemented as a deformation information calculation module that reads two images from the memory, and calculates the deformation information that represents the deformation between the two images. The feature area detection section 106 is implemented as a feature area detection module that reads the first to Nth images from the memory, and performs the feature area detection process on each of the first to Nth images. The identicalness determination section 109 is implemented as an identicalness determination module that reads the ith feature area, the (i+1)th feature area, and the deformation information h(i, i+1) from the memory, and performs the identicalness determination process on the ith deformation area and the (i+1)th feature area. The summarization processing section 113 is implemented as a summarization processing module that reads the results of the identicalness determination process from the memory, and performs the image summarization process on the image sequence based on the results of the identicalness determination process. The deformation estimation processing section 108 is implemented as a deformation estimation module that reads the ith feature area and the deformation information h(i, i+1) from the memory, and projects the ith feature area onto the (i+1)th image based on the ith feature area and the deformation information h(i, i+1) to calculate the ith deformation area.

3. Second Embodiment

The second embodiment is described below. As illustrated in FIG. 5 (see the third image), the feature area that corresponds to the object OB2 may not be detected within the image Y3 although the object OB2 is captured within the image X3. Such a situation may occur when the feature area within an in vivo image is screened by the contents, the fold structure, or the like (see above), for example.

The method according to the first embodiment performs the deformation estimation process on the feature area to calculate the deformation area within the contiguous image, compares the deformation area and the feature area detected within the contiguous image, and terminates the identicalness determination process on the processing target feature area when the degree of similarity is low. Specifically, when a feature area that corresponds to the deformation area FA'1-3 is not found within the image Y4, the process performed on the feature area FA1-1 is terminated (see FIG. 4).

In this case, even when an identical object is continuously captured (see the object OB2 included in the images X2 to X5), the process performed on the feature area that corresponds to the object OB2 is terminated at a timing at which the feature area that corresponds to the object OB2 has not been detected. Such a situation also occurs when the feature area detection process has failed, and when the object OB2 is not captured within the image X3. Specifically, when a feature area that corresponds to the deformation area FA'2-2 is not found within the image Y3, the process performed on the feature area FA2-2 is terminated (see FIG. 5). Therefore, the feature area FA2-4 within the image Y4 and the feature area FA2-5 within the image Y5 are determined to differ from the feature area FA2-2 although the feature area FA2-4 and the feature area FA2-5 are identical to the feature area FA2-2. As a result, the second image, the fourth image, and the fifth image illustrated in FIG. 5 are divided into two identical feature area image groups although the second image, the fourth image, and the fifth image can be set to be a single identical feature area image group. This increases the number of images selected as the representative image (i.e., the number of images included in the summary image sequence), and reduces the effect of reducing the burden imposed on the user.

According to the second embodiment, even when a feature area that is determined to be identical to a given feature area has not been found by the identicalness determination process, the identicalness determination process on the given feature area is continuously performed corresponding to a given number of images. According to this configuration, even when a feature area cannot be temporarily detected (see the image Y3) during the identicalness determination process, the process on the feature area FA2-2 is continuously performed on the fourth image and the fifth image, and the feature area FA2-2 and the feature areas FA2-4 and FA2-5 are determined to be identical to each other.

A specific example is described below with reference to FIG. 8. Note that the objects OB1 and OB2 and the detected feature areas are the same as those illustrated in FIG. 4 and the like.

The feature area FA2-2 is detected within the second image, and the identicalness determination process that searches an image that includes a feature area that is identical to the feature area FA2-2 is performed. In this case, the deformation estimation process is performed on the feature area FA2-2 using the deformation information h(2, 3) to calculate a deformation area FA$^{(1)}$2-2 (see the first embodiment). Note that the deformation area FA$^{(1)}$2-2 is the same as the deformation area FA'2-2 illustrated in FIG. 5. It is then determined that the image Y3 does not include a feature area that is identical to the deformation area FA$^{(1)}$2-2 in the same manner as in the example illustrated in FIG. 5.

In the second embodiment, whether or not the next image includes a feature area that is identical to the feature area FA2-2 is then determined instead of terminating the process. However, since a feature area that corresponds to the object OB2 has not been detected within the image Y3, it is impossible to perform the deformation estimation process on a feature area detected within the third image to calculate a deformation area within the fourth image.

Therefore, the feature area FA2-2 is deformed and projected onto the fourth image, and compared with the feature area detected within the image Y4. The area obtained by projecting the feature area FA2-2 onto the fourth image can be calculated using the deformation information h(2, 4) about the image X2 and the image X4, and the feature area FA2-2. However, the deformation information about two arbitrary images can be calculated (represented) using a combination of the deformation information about contiguous images therebetween. Specifically, an area calculated by deforming the feature area FA2-2 using the deformation information h(2, 4) is equal to an area calculated by deforming the feature area FA2-2 using the deformation information h(2, 3), and deforming the resulting area using the deformation information h(3, 4). Since the deformation area FA$^{(1)}$2-2 has been calculated by deforming the feature area FA2-2 using the deformation information h(2, 3), the deformation area FA$^{(1)}$2-2 is deformed using the deformation information h(3, 4) to calculate a deformation area FA$^{(2)}$2-2.

Figure 8:
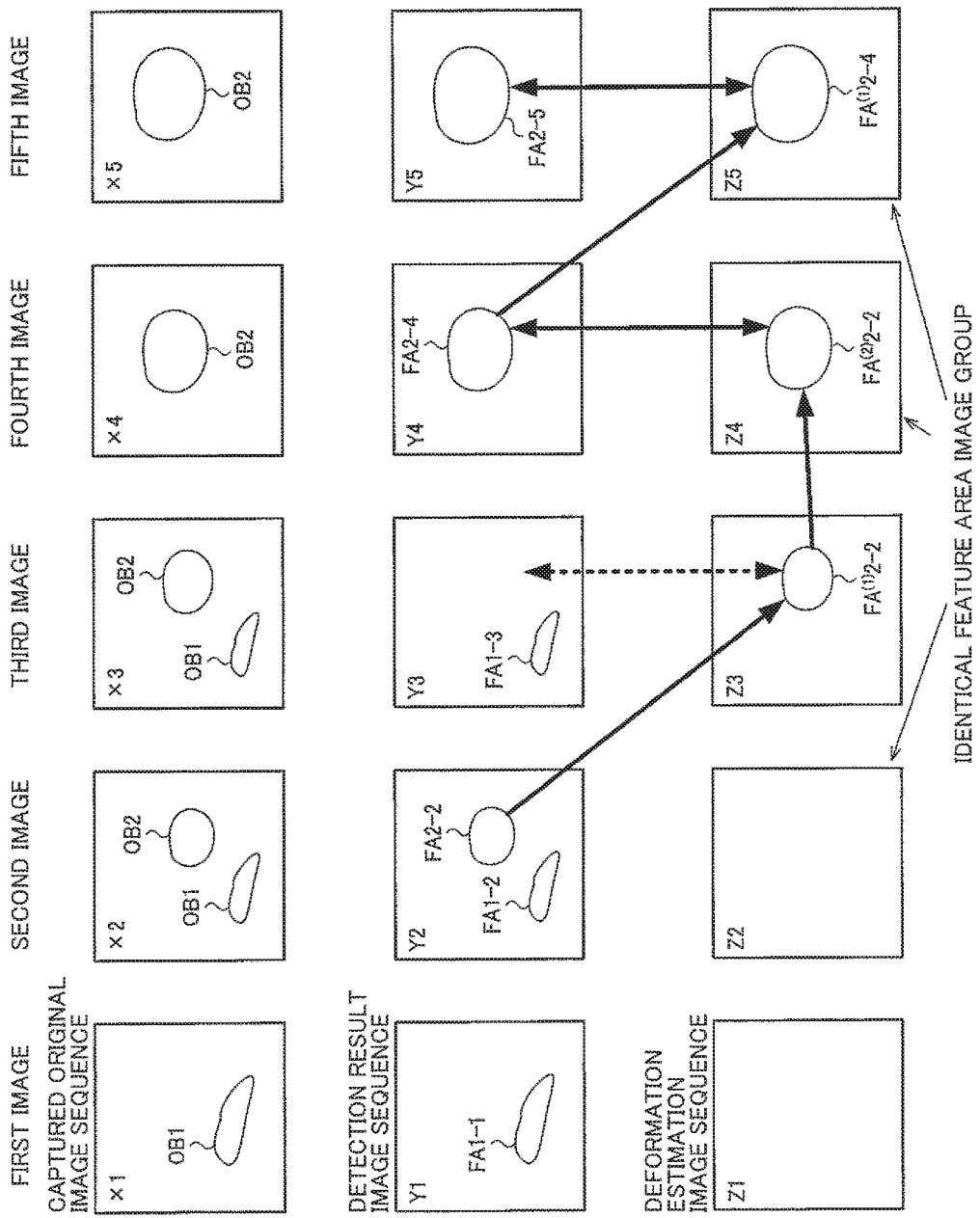
FIG. 8 is a view illustrating a method (second embodiment).

In the example illustrated in FIG. 8, the feature areas FA2-2 and FA2-4 are determined to be identical to each other since the degree of similarity between the deformation area FA$^{(1)}$2-2 and the feature area FA2-4 is high. After a feature area that is identical to the feature area (e.g., feature area FA2-2) used as the starting point has been found, the latest feature area (e.g., feature area FA2-4) is deformed and projected onto the contiguous image in the same manner as described above in connection with the first embodiment.

In the example illustrated in FIG. 8, a feature area that is identical to the feature area used as the starting point has been found in the third image with respect to the second image. When a feature area that is identical to the feature area used as the starting point has not been found, a feature area that is identical to the feature area used as the starting point is searched corresponding to a given number of images. For example, a threshold value Th is set in advance, and the identicalness determination process is performed up to the (i+Th)th image when a feature area that is identical to the feature area used as the starting point has been found up to the ith image, and has not been found in the (i+1)th and subsequent images. When a feature area that is identical to the feature area used as the starting point has been found in an image that precedes the (i+Th)th image, the identicalness determination process is similarly performed from the image in which a feature area that is identical to the feature area used as the starting point has been found. In this case, the feature area FAi within the ith image is sequentially deformed using the deformation information to calculate deformation areas $FA^{(1)}i$, $FA^{(2)}i$, ..., and $FA^{(Th)}i$, and compared with the detected feature area. When a feature area that is identical to the feature area used as the starting point has not been found up to the (i+Th)th image, it is determined that a feature area that is identical to the processing target feature area is not present within the (i+1)th and subsequent images, and the identicalness determination process performed on the processing target feature area is terminated.

Figure 9:
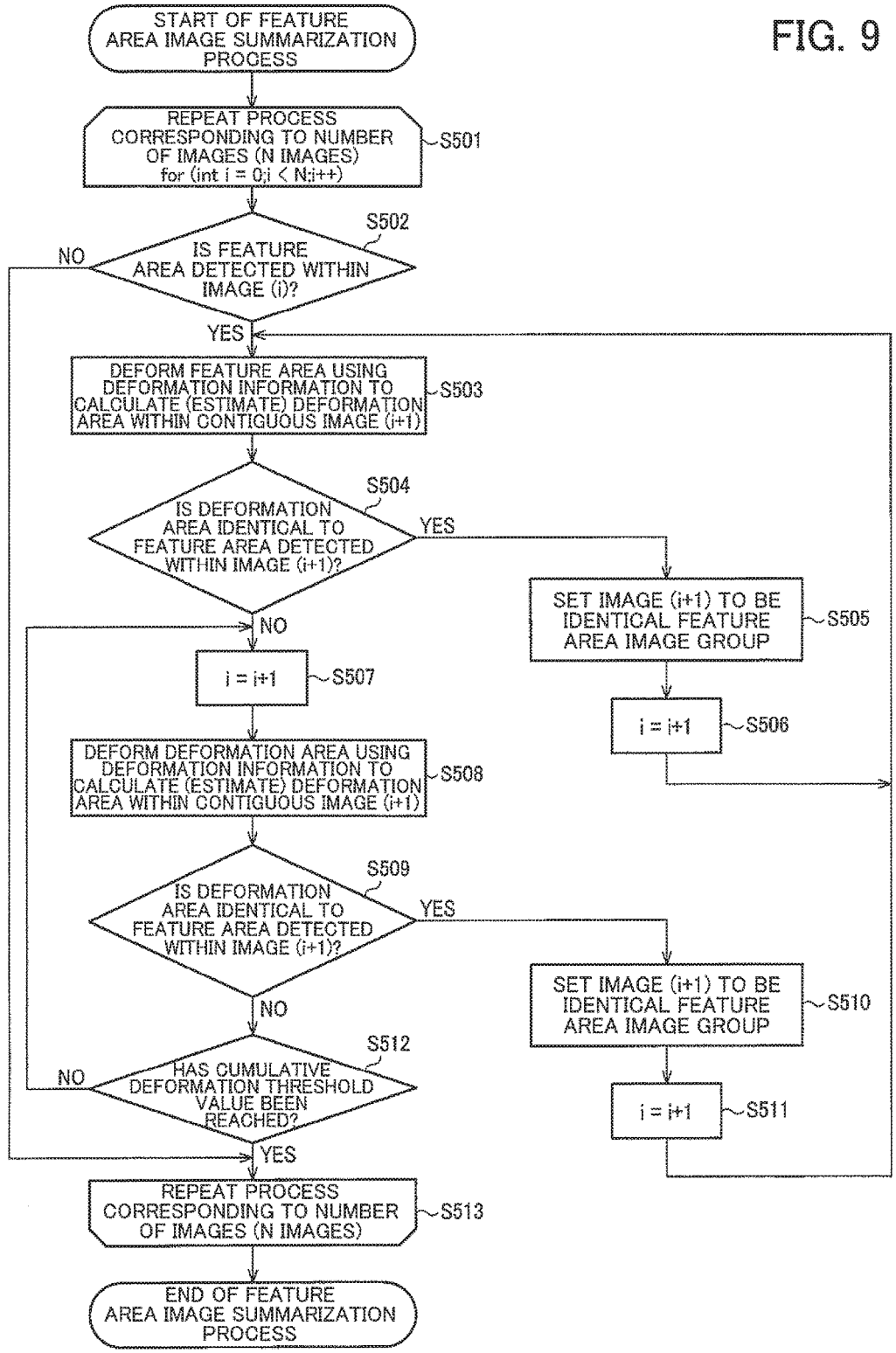
FIG. 9 is a flowchart illustrating a process (second embodiment).

FIG. 9 is a flowchart illustrating the process according to the second embodiment. Note that steps S501 and S513 illustrated in FIG. 9 are the same as the steps S301 and S307 illustrated in FIG. 6 (i.e., the process is repeated corresponding to the number of images included in the image sequence). Steps S502 and S503 illustrated in FIG. 9 are the same as the steps S302 and S303 illustrated in FIG. 6.

In a step S504, the deformation area and the feature area detected within the contiguous image are compared in the same manner as in the step S304. When the deformation area and the feature area detected within the contiguous image are identical to each other (Yes in S504), steps S505 and S506 are performed. The steps S505 and S506 are the same as the steps S305 and S306 illustrated in FIG. 6.

The process performed when it has been determined that the deformation area and the feature area detected within the contiguous image are not identical to each other (No in S504) is described below. In the first embodiment, when it has been determined that the deformation area and the feature area detected within the contiguous image are not identical to each other (No in S304) (see FIG. 6), the process performed on the image (i) in the step S302 is terminated. In the second embodiment, the identicalness determination process is further performed on the next image. Specifically, the value i is incremented (S507), and the deformation estimation process is performed on the deformation area calculated by the step S503 using the deformation information to calculate a deformation area within the contiguous image (S508). In the example illustrated in FIG. 8, the deformation area $FA^{(1)}2-2$ is deformed using the deformation information h(3, 4) to calculate the deformation area $FA^{(2)}2-2$.

The deformation area calculated by the step S508 and the feature area detected within the image (i+1) (i.e., contiguous image) are compared (S509). Note that the contiguous image (i+1) used in the step S509 differs from the contiguous image (i+1) used in the step S504 since the value i has been incremented in the step S507.

When it has been determined that the deformation area and the feature area detected within the contiguous image are identical to each other (Yes in S509), it is determined that the contiguous image (i+1) includes a feature area that is identical to the feature area included in the image (i) (see S502), and the contiguous image (i+1) is set to be the identical feature area image group (S510). The value i is then incremented (S511), and the step S503 is performed again (i.e., the identicalness determination process is further performed).

When it has been determined that the deformation area and the feature area detected within the contiguous image are not identical to each other (No in S509), the number of search target images (see S507) is compared with the cumulative deformation threshold value (S512). When the number of search target images is equal to or less than the threshold value, the step S507 is performed again (i.e., the process is further performed on the next image). When the number of search target images exceeds the threshold value, the step S501 is performed again to update the image used as the starting point of the process.

Note that a plurality of feature areas may be detected from one image. In this case, the process is performed in parallel on each feature area in the same manner as in the first embodiment. Specifically, the steps S405 and S407 illustrated in FIG. 7 are replaced by the steps S503 to S512 (i.e., the process according to the second embodiment) illustrated in FIG. 9.

According to the second embodiment, even when it has been determined that the deformation area and the detected feature area are not identical to each other, the deformation estimation process is cumulatively performed on the deformation area corresponding to the number of images that corresponds to the threshold value. Therefore, when it has been determined that the deformation area and the detected feature area are identical to each other before the number of images that corresponds to the threshold value has been reached, discontinuous images can be set to be the identical feature area image group even when the feature area has not been continuously detected.

According to the second embodiment, when the identicalness determination section 109 has determined that an identical feature area has not been captured, the identicalness determination section 109 may continue the process based on the deformation information corresponding to a given number of images, and perform the identicalness determination process when the feature area has been detected within an image among a preset number of images.

In the example illustrated in FIG. 8, even when a feature area that is identical to the feature area FA2-2 has not been detected from the third image as a result of comparing the deformation area $FA^{(1)}2-2$ within the image Z3 and the feature area detected within the image Y3, the process performed on the feature area FA2-2 is continuously performed, and the identicalness determination process is performed using the deformation area $FA^{(2)}2-2$ within the fourth image Z4 and the feature area FA2-4 detected within the image Y4.

According to this configuration, even when a feature area that is identical to the processing target feature area has not been detected within some of the consecutive images (see the third image (X3, Y3) illustrated in FIG. 8), it is possible to continue the identicalness determination process using the next image instead of terminating the process. According to the first embodiment, the process performed on the feature area FA2-2 is terminated when the process has been performed on the third image (see FIG. 5), and the identicalness determination process is not performed on the feature areas FA2-4 and FA2-5 that are identical to the feature area FA2-2. Therefore, since only the second image is set to be the identical feature area image group with respect to the second image, the effect of reducing the number of images may decrease. According to the second embodiment, however, the identicalness determination process is performed on the feature area FA2-2 and the feature areas FA2-4 and FA2-5 (see FIG. 8). Therefore, since the second image, the fourth image, and the fifth image are set to be the identical feature area image group, it is possible to improve the effect of reducing the number of images as compared with the method according to the first embodiment, and further reduce the burden imposed on the user.

When the identicalness determination section 109 has determined that the ith feature area and the (i+1)th feature area are not identical to each other since a feature area has not been detected from the (i+1)th image, the identicalness determination section 109 may perform the identicalness determination process on the ith feature area and the (i+2)th feature area based on the ith feature area, the (i+3)th feature area, and the deformation information h(i, i+2) about the ith image and the (i+2)th image, the (i+2)th feature area being detected as a result of the feature area detection process performed on the (i+2)th image.

According to this configuration, even when a feature area that is identical to the ith feature area has not been found within the contiguous image, it is possible to perform the identicalness determination process on the ith feature area and the feature area within the non-contiguous image by cumulatively performing the deformation estimation process on the ith feature area. Specifically, the deformation estimation process is performed on the ith feature area (e.g., the feature area FA2-2 illustrated in FIG. 8) to calculate a deformation area (deformation area FA$^{(2)}$2-2) within the third image with respect to the image that includes the ith feature area, and the deformation area and the feature area (feature area FA2-4) detected within the third image are compared.

Note that the process that calculates the deformation area FA$^{(2)}$2-2 need not be performed using the feature area FA2-2 and the deformation information h(2, 4) (see above). The process that calculates the deformation area FA$^{(2)}$2-2 is performed by performing the deformation estimation process on the deformation area FA$^{(2)}$2-2 using the deformation information h(3, 4). Specifically, the deformation estimation processing section 108 included in the image processing device may perform the deformation estimation process that projects the (i+1)th deformation area onto the (i+2)th image based on the (i+1)th deformation information about the (i+1)th image and the (i+2)th image to calculate the (i+2)th deformation area, and the identicalness determination section 109 may perform the identicalness determination process on the ith feature area and the (i+2)th feature area based on the (i+2)th deformation area and the (i+2)th feature area detected as a result of the feature area detection process performed on the (i+2)th image.

The identicalness determination section 109 may terminate the identicalness determination process on the ith feature area when the identicalness determination section 109 has determined that the ith feature area and an (i+k)th (k is an integer) feature area are not identical to each other, and k≥Th (Th is a given integer), the (i+k)th feature area being detected as a result of the feature area detection process performed on the (i+k)th image. The identicalness determination section 109 may perform the identicalness determination process on the ith feature area and an (i+k+1)th feature area based on the ith feature area, the (i+k+1)th feature area, and the deformation information h(i, i+k+1) about the ith image and an (i+k+1)th image when the identicalness determination section 109 has determined that the ith feature area and the (i+k)th feature area are not identical to each other, and k<Th, the (i+k+1)th feature area being detected as a result of the feature area detection process performed on the (i+k+1)th image.

This makes it possible to continue the process corresponding to a given number of images (Th images in the above example) when identical feature areas have not been found instead of performing the process up to the third image. Therefore, even when a non-detection period (in which the feature area is not detected) occurs up to Th frames, it is possible to perform the identicalness determination process on the feature area at a timing that precedes or follows the non-detection period. Even when the feature area detection accuracy is not sufficient, it may be possible to detect the feature area when the imaging conditions have been changed. When the feature area is screened by the contents, the fold structure, or the like, it may be possible to detect the feature area when the contents have been moved (removed in a narrow sense), or the fold structure has moved due to its motion. Specifically, it is useful to continue the process over a certain number of frames (instead of terminating the process when the feature area has not been detected in one frame) in order to find identical feature areas. Note that the identicalness determination process on the current processing target feature area is terminated when identical feature areas have not been found as a result of performing the identicalness determination process on a give number of images. In such a case, it is likely that the processing target feature area lies outside the imaging range (e.g., when the capturing target object range changes to a large extent), and it may be useless to continue the process.

The first embodiment and the second embodiment to which the invention is applied, and the modifications thereof, have been described above. Note that the invention is not limited to the first embodiment, the second embodiment, and the modifications thereof. The elements may be modified in various ways within the scope of the invention when implementing the invention. A plurality of elements described above in connection with the first embodiment, the second embodiment, and the modifications thereof may be appropriately combined to implement various configurations. For example, some elements may be omitted from the elements described above in connection with the first embodiment, the second embodiment, and the modifications thereof. The elements described above in connection with different embodiments or modifications may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An image processing device comprising:
a memory that stores information; and
a processor that operates based on the information stored in the memory, the processor comprising hardware, the processor being configured to implement:
an image sequence acquisition process that acquires an image sequence that includes first to Nth (N is an integer equal to or larger than 2) consecutive images;
a deformation information calculation process that calculates deformation information that represents deformation between two images included in the image sequence;
a feature area detection process that detects a feature area from each of the first to Nth images;
an identicalness determination process that determines whether or not an ith feature area and an (i+1)th feature area are identical to each other based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image;
and
a deformation estimation process that projects the ith feature area onto the (i+1)th image based on the ith feature area and the deformation information h(i, i+1) to calculate an ith deformation area,
wherein the processor is configured to implement the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area, and implement the identicalness determination process that determines whether or not the ith feature area and the (i+1)th feature area are identical to each other based on the ith deformation area obtained by the deformation estimation process and the (i+1)th feature area, and
wherein the processor is further configured to implement:
a summarization process that summarizes the image sequence based on results of the identicalness determination process to generate a summary image sequence consisting of fewer than N images; and
an output process that outputs the summary image sequence generated by the summarization process.

2. The image processing device as defined in claim 1, wherein the processor is configured to implement the image sequence acquisition process that acquires a plurality of time-series in vivo images as the image sequence, and
the processor is configured to implement the feature area detection process that detects at least one of a lesion area and an abnormal mucous membrane area within each of the plurality of time-series in vivo images as the feature area.

3. The image processing device as defined in claim 2, wherein the processor is configured to implement the deformation information calculation process that calculates the deformation information based on the ith deformation estimation target area that includes at least a normal mucous membrane area within the ith image, and the (i+11)th deformation estimation target area that includes at least the normal mucous membrane area within the (i+11)th image.

4. The image processing device as defined in claim 1, wherein, when the processor has determined that an identical feature area has not been captured in the identicalness determination process, the processor is configured to implement the identicalness determination process that continues a process based on the deformation information corresponding to a given number of images, and performs the identicalness determination process when the feature area has been detected within an image among a preset number of images.

5. The image processing device as defined in claim 1, wherein, when processor has determined that the ith feature area and the (i+1)th feature area are not identical to each other since the feature area has not been detected from the (i+1)th image in the identicalness determination process, the processor is configured to implement the identicalness determination process that performs the identicalness determination process on the ith feature area and an (i+2)th feature area based on the ith feature area, the (i+2)th feature area, and the deformation information h(i, i+2) about the ith image and an (i+2)th image, the (i+2)th feature area being detected as a result of the feature area detection process performed on the (i+2)th image.

6. The image processing device as defined in claim 5, wherein:
the processor is configured to implement the identicalness determination process that terminates the identicalness determination process on the ith feature area when the identicalness determination process has determined that the ith feature area and an (i+k)th (k is an integer) feature area are not identical to each other, and k≥Th (Th is a given integer), the (i+k)th feature area being detected as a result of the feature area detection process performed on the (i+k)th image, and
the processor is configured to implement the identicalness determination process that performs the identicalness determination process on the ith feature area and an (i+k+1)th feature area based on the ith feature area, the (i+k+1)th feature area, and the deformation information h(i, i+k+1) about the ith image and an (i+k+1)th image when the identicalness determination process has determined that the ith feature area and the (i+k)th feature area are not identical to each other, and k<Th, the (i+k+1)th feature area being detected as a result of the feature area detection process performed on the (i+k+1)th image.

7. The image processing device as defined in claim 1, wherein the processor is configured to implement the deformation information calculation process that calculates a motion vector at at least one position within an image as the deformation information, and
the processor is configured to implement the identicalness determination process that performs the identicalness determination process on the ith feature area and the (i+1)th feature area based on the ith feature area, the (i+1)th feature area, and the inter-image motion vector between the ith image and the (i+1)th image.

8. The image processing device as defined in claim 1, wherein the processor is configured to implement the identicalness determination process that performs the identicalness determination process based on at least one piece of information among shape information, color information, texture information, and intra-image position information about the ith deformation area that is an area obtained by projecting the ith feature area onto the (i+1)th image using the deformation information h(i, i+1), and the (i+1)th feature area.

9. The image processing device as defined in claim 1, wherein the processor is configured to implement the identicalness determination process that performs the identicalness determination process on the ith feature area and the (i+1)th feature area based on reliability of the deformation information h(i, i+1).

10. The image processing device as defined in claim 1, wherein the processor is configured to implement the summarization processing process that includes:
an image group setting process that sets an identical feature area image group that includes images among the first to Nth images for which it has been determined that an identical feature area is captured based on the results of the identicalness determination process; and
a summary image sequence generation process that generates the summary image sequence by selecting at least one representative image from the identical feature area image group that has been set by the image group setting process.

11. The image processing device as defined in claim 10, wherein the processor is configured to implement the summarization processing process that selects the representative image based on at least one piece of information among area information about the feature area, color information about the feature area, texture information about the feature area, intra-image position information about the feature area, and reliability information about the feature area detection process that correspond to each image included in the identical feature area image group.

12. An image processing method for an image processing device comprising a memory that stores information, and a processor that operates based on the information stored in the memory, the processor comprising hardware, the method comprising, by the processor:
 acquiring an image sequence that includes first to Nth (N is an integer equal to or larger than 2) consecutive images;
 performing a deformation information calculation process that calculates deformation information that represents deformation between two images included in the image sequence;
 performing a feature area detection process on each of the first to Nth images that detects a feature area from each of the first to Nth images;
 performing an identicalness determination process that determines whether or not an ith feature area and an (i+1)th feature area are identical to each other, based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image; and
 performing a deformation estimation process that projects the ith feature area onto the (i+1)th image based on the ith feature area and the deformation information h(i, i+1) to calculate an ith deformation area;
wherein:
 the deformation information calculation process that calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area;
 the identicalness determination process is performed on the ith feature area and the (i+1)th feature area based on the ith deformation area obtained by the deformation estimation process and the (i+1)th feature area; and
 the method further comprises:
  performing an image summarization process on the image sequence based on results of the identicalness determination process to generate a summary image sequence consisting of fewer than N images; and
  performing an output process that outputs the summary image sequence generated by the summarization process.

13. A non-transitory computer-readable storage device having stored thereon a program that is executable by a microprocessor to cause the microprocessor to perform functions comprising:
 acquiring an image sequence that includes first to Nth (N is an integer equal to or larger than 2) consecutive images;
 performing a deformation information calculation process that calculates deformation information that represents deformation between two images included in the image sequence;
 performing a feature area detection process that detects a feature area from each of the first to Nth images;
 performing an identicalness determination process that determines whether or not an ith feature area and an (i+1)th feature area are identical to each other based on the ith feature area, the (i+1)th feature area, and the deformation information h(i, i+1) about an ith image and an (i+1)th image, the ith feature area being detected as a result of the feature area detection process performed on the ith image, and the (i+1)th feature area being detected as a result of the feature area detection process performed on the (i+1)th image; and
 performing a deformation estimation process that projects the ith feature area onto the (i+1)th image based on the ith feature area and the deformation information h(i, i+1) to calculate an ith deformation area;
wherein:
 the deformation information calculation process calculates the deformation information h(i, i+1) based on an ith deformation estimation target area that includes at least an area of the ith image other than the ith feature area, and an (i+1)th deformation estimation target area that includes at least an area of the (i+1)th image other than the (i+1)th feature area;
 the identicalness determination process determines whether or not the ith feature area and the (i+1)th feature area are identical to each other based on the ith deformation area obtained by the deformation estimation process and the (i+1)th feature area; and
 the program causes the microprocessor to perform further functions comprising:
  performing a summarization process that summarizes the image sequence based on results of the identicalness determination process to generate a summary image sequence consisting of fewer than N images; and
  performing an output process that outputs the summary image sequence generated by the summarization process.

* * * * *